US008608808B2

(12) United States Patent
Rondot et al.

(10) Patent No.: US 8,608,808 B2
(45) Date of Patent: Dec. 17, 2013

(54) COMPOSITION FOR DYEING KERATIN FIBERS, INCLUDING AT LEAST ONE ORTHO-DIPHENOL DERIVATIVE, ONE PARTICULAR METAL DERIVATIVE, AND ONE ALKALINIZING AGENT

(75) Inventors: Christophe Rondot, Mitry-Mory (FR); Stéphane Sabelle, Paris (FR); Alexandre Cavezza, Les Pavillons sous Bois (FR); Franco Manfre, Le Perreux sur Marne (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/518,862

(22) PCT Filed: Dec. 21, 2010

(86) PCT No.: PCT/FR2010/052841
§ 371 (c)(1),
(2), (4) Date: Feb. 13, 2013

(87) PCT Pub. No.: WO2011/086282
PCT Pub. Date: Jul. 21, 2011

(65) Prior Publication Data
US 2013/0139846 A1 Jun. 6, 2013

Related U.S. Application Data

(60) Provisional application No. 61/300,117, filed on Feb. 1, 2010.

(30) Foreign Application Priority Data

Dec. 23, 2009 (FR) ...................... 09 59515

(51) Int. Cl.
*A61Q 5/10* (2006.01)
(52) U.S. Cl.
USPC ................ 8/405; 8/406; 8/407; 8/424; 8/435; 132/202; 132/208
(58) Field of Classification Search
USPC .............. 8/405, 406, 407, 424, 435; 132/202, 132/208
See application file for complete search history.

(56) References Cited

U.S. PATENT DOCUMENTS

| 3,376,110 | A | | 4/1968 | Shiraeff |
|---|---|---|---|---|
| 3,931,249 | A | | 1/1976 | Stautzenberger |
| 4,412,934 | A | | 11/1983 | Chung et al. |
| 4,690,685 | A | * | 9/1987 | Grollier et al. ............... 8/405 |
| 4,823,985 | A | | 4/1989 | Grollier et al. |
| 5,008,093 | A | | 4/1991 | Merianos |
| 5,183,901 | A | | 2/1993 | Login et al. |
| 5,603,734 | A | | 2/1997 | Prota et al. |
| 6,953,486 | B2 | | 10/2005 | Pruche |
| 2003/0103917 | A1 | | 6/2003 | Pruche |

FOREIGN PATENT DOCUMENTS

| EP | 0664114 | 7/1995 |
|---|---|---|
| FR | 2586913 | 3/1987 |
| FR | 2814943 | 4/2002 |
| FR | 2814945 | 4/2002 |
| FR | 2814946 | 4/2002 |
| FR | 2814947 | 4/2002 |
| WO | 9500625 | 1/1995 |

OTHER PUBLICATIONS

English language abstract of FR 2 814 945, (2002).
Eckert, "Niobium and niobium compounds," Ulmann's Encyclopedia of Industrial Chemistry, 2012 Wiley-VCH Verlag GmbH & Co. KGaA, Weinheim, vol. 24, pp. 133-147, DOI: 10.1002/14356007.a17_251.
Felix, "Indium and Indium Compounds," Ulmann's Encyclopedia of Industrial Chemistry, 2012 Wiley-VCH Verlag GmbH & Co. KGaA, Weinheim, vol. 19, pp. 65-74, DOI: 10.1002/14356007.a14_157.
Gauglitz, "Ultraviolet and Visible Spectroscopy," Ulmann's Encyclopedia of Industrial Chemistry, 2012 Wiley-VCH Verlag GmbH & Co. KGaA, Weinheim, vol. 37, pp. 599, DOI: 10.1002/14356007.b05_383.
Graf, "Tin, Tin Alloys, and Tin Compounds," Ullmann's Encyclopedia, 2005 Wiley-VCH Verlag GmbH & Co. KGaA, Weinheim, pp. 1-35, DOI: 10.1002/14356007.a27_049.
Grychtol & Mennicke, "Metal-Complex Dyes," Ullmann's Encyclopedia of Industrial Chemistry, 2012 Wiley-VCH Verlag GmbH & Co. KGaA, Weinheim, vol. 22, pp. 595-633, DOI: 10.1002/14356007.a16_299.
Hudson et al., "Aluminum Oxide," Ullmann's Encyclopedia of Industrial Chemistry, 2012 Wiley-VCH Verlag GmbH & Co. KGaA, Weinheim, vol. 2, pp. 607-645, DOI: 10.1002/14356007.a01_557.
Hunger & Herbst, "Pigments, Organic," 2005 Wiley-VCH Verlag GmbH & Co. KGaA, Weinheim, pp. 1-46, DOI: 10.1002/14356007.a20_371.
Lobbert, "Phthalocyanines," Ullmann's Encyclopedia of Industrial Chemistry, 2012 Wiley-VCH Verlag GmbH & Co. KGaA, Weinheim, vol. 27, pp. 181-213, DOI: 10.1002/14356007.a20_213.
Murray, "Clays," Ulmann's Encycopedia of Industrial Chemistry, 2006 Wiley-VCH Verlag GmbH & Co. KGaA, Weinheim, pp. 1-34, DOI: 10.1002/14356007.a07_109.
Neilsen & Wilfing, "Zirconium and Zirconium Compounds," Ullmann's Encyclopedia of Industrial Chemistry, 2012 Wiley VCH Verlag GmbH & Co. KGaA, Weinheim, vol. 39, pp. 753-778, DOI: 10.1002.14356007.a28_543.
Pfoertner, "Photochemistry," Ullmann's Encyclopedia, 2005 Wiley-VCH Verlag GmbH & Co. KGaA, Weinheim, pp. 1-29, DOI: 10.1002/14356007.a19_573.

(Continued)

*Primary Examiner* — Eisa Elhilo
(74) *Attorney, Agent, or Firm* — O'Brien Jones PLLC

(57) ABSTRACT

A subject-matter of the invention is a composition comprising a) at least one ortho-diphenol derivative, b) at least one specific metal derivative and c) at least one basifying agent, a method for dyeing keratinous fibers by treatment of the said fibers using the ingredients a), b) et c) and the use thereof for dyeing keratinous fibers. This hair dyeing method makes it possible to obtain better colorations which are more uniform, chromatic and lasting and which do not detrimentally affect the cosmetic properties of the keratinous fibers, starting from an extract of ortho-diphenols which are in particular natural.

20 Claims, No Drawings

(56) References Cited

OTHER PUBLICATIONS

Reinhardt & Winkler, "Cerium Mischmetal, Cerium Alloys, and Cerium Compounds," Ullmann's Encyclopedia of Industrial Chemistry, 2012 Wiley-VCH Verlag GmbH & Co. KGaA, Weinheim, vol. 8, pp. 41-56 DOI: 10.1002/14356007.a06_139.

Sebenik et al., "Molybdenum and Molybdenum Compounds," Ullmann's Encyclopedia 2005 Wiley-VCH Verlag GmbH & Co. KGaA, Weinheim, pp. 1-47, DOI: 10.1002/14356007.a16_655.

Sibum et al., "Titanium, Titanium Alloys, and Titanium Compounds," Ullmann's Encyclopedia of Industrial Chemistry, 2012 Wiley-VCH Verlag GmbH & Co. KGaA, Weinheim, vol. 37, pp. 51-82, DOI: 10.1002/14356007.a27_095.

Van Den Hoek et al., "Lamps," Ullmann's Encyclopedia, 2005 Wiley-VCH Verlag GmbH & Co. KGaA, Weinheim, pp. 1-40, DOI: 10.1002/14356007.a15_115.

Vankar et al., "Ecofriendly sonicator dyeing of cotton with *Rubia cordifolia* Linn. using biomordant," Dyes and Pigments, 76:207-212 (2008).

Whiting, "Natural phenolic compounds 1900-2000: a bird's eye view of a century's chemistry," Nat. Prod. Rep., 18:583-606 (2001).

\* cited by examiner

COMPOSITION FOR DYEING KERATIN FIBERS, INCLUDING AT LEAST ONE ORTHO-DIPHENOL DERIVATIVE, ONE PARTICULAR METAL DERIVATIVE, AND ONE ALKALINIZING AGENT

This is a national stage application of PCT/FR2010/052841, filed internationally on Dec. 21, 2010, which claims the benefit of U.S. Provisional Application No. 61/300,117, filed on Feb. 1, 2010, and claims priority to French Application No. 0959515, filed on Dec. 23, 2009.

A subject-matter of the invention is a composition comprising a) at least one ortho-diphenol derivative, b) at least one specific metal derivative and c) at least one basifying agent, a method for dyeing keratinous fibres by treatment of the said fibres using the ingredients a), b) et c) and the use thereof for dyeing keratinous fibres.

It is known to obtain "permanent" colorations with dyeing compositions comprising oxidation dye precursors, generally known as oxidation bases, such as ortho- or para-phenylene-diamines, ortho- or para-aminophenols and heterocyclic compounds. These oxidation bases are colourless or weakly coloured compounds which, in combination with oxidizing products, can give rise to coloured compounds by an oxidative condensation process. It is also known that the shades obtained can be varied by combining these oxidation bases with couplers or coloration modifiers, the latter being chosen in particular from aromatic meta-diamines, meta-aminophenols, meta-diphenols and certain heterocyclic compounds, such as indole compounds. This oxidation dyeing method consists in applying, to the keratinous fibres, bases or a mixture of bases and couplers with hydrogen peroxide ($H_2O_2$ or aqueous hydrogen peroxide solution), as oxidizing agent, in leaving to diffuse, and in then rinsing the fibres. The colorations resulting therefrom are permanent, strong and resistant to external agents, in particular to light, bad weather, washing operations, perspiration and rubbing actions.

However, the commercial hair dyes which comprise them can have drawbacks, such as staining, and problems of odour, comfort and damage to the keratinous fibres. This is particularly the case with oxidation dyeing operations.

In the field of dyeing, it is also known to dye keratinous substances, such as the hair or the skin, starting from ortho-diphenol compounds in the presence of a metal salt, in particular a Mn and/or Zn salt. In particular, Patent Applications FR 2 814 943, FR 2 814 945, FR 2 814 946 and FR 2 814 947 propose compositions for dyeing the skin or keratinous fibres, comprising a dye precursor which comprises at least one ortho-diphenol, Mn and/or Zn oxides and salts, alkaline agents of hydrogencarbonate type in a specific Mn, Zn/hydrogencarbonate ratio, and optionally an enzyme. According to these documents, it is possible to obtain colorations of keratinous substances with atmospheric oxygen. However, the colorations obtained are not strong enough, in particular in the case of hair fibres.

It is also known to use metals to improve the coloration of the hair in amounts of metals of the same order of magnitude as that of the dyes on using a mordanting method. Nevertheless, this process generally exhibits the drawback of not always respecting the cosmetic appearance of the keratinous fibre.

In addition, it is known to use an ortho-diphenol, such as 4-methylcatechol, and a copper salt of copper acetate type to dye the hair with persulfate (EP 0 664 114). Nevertheless, the colorations obtained are not entirely satisfactory, in particular in terms of homogeneity of the coloration, the chromaticity and/or the absorption of the colour.

There thus exists a real need to develop dyeing methods which make it possible to obtain powerful colorations starting from ortho-diphenols, in particular starting from a natural extract rich in ortho-diphenols, while limiting the bleaching of keratinous fibres. In particular, there exists a need to obtain colorations which are less aggressive for the hair, and which are simultaneously resistant to external agents (light, bad weather and shampooing operations), which are lasting and/or uniform, with little selectivity of coloration between the root and the end, while remaining powerful and/or chromatic. It is also desirable for the colorations obtained to remain natural, in particular in golden highlights.

This aim is achieved by the present invention, a subject-matter of which is a method for dyeing keratinous fibres, in which the said fibres are treated with:

a) one or more ortho-diphenol derivative(s), in particular different from the derivatives comprising indole units, b) one or more metal derivative(s) chosen from metal salts, metal complexes, metal oxides, metal oxoanions, their supported forms, their hydrates and their mixtures for which the metal or metals is (are) chosen from:
  i) gold (Au),
  ii) molybdenum (Mo),
  iii) silver (Ag)(I) and (II) oxides, Ag(I) and (II) salts chosen from silver halides, Ag sulfate, $[R^1-C(O)O]_n$ Ag with n=1 or 2, $R^1$ representing a ($C_1$-$C_6$)alkyl group, such as Ag acetate, Ag lactate, silver complexes, such as Ag(I) metalloporphyrins, Ag(I) phthalocyanines or Ag(I) chlorophyllins,
  iv) tungsten (W),
  v) vanadium (V),
  vi) ruthenium (Ru),
  vii) magnesium (Mg)(II) oxide, Mg(II) salts chosen from Mg sulfate, Mg(II) metalloporphyrins, Mg(II) phthalocyanines, Mg(II) chlorophyllins or Mg(II) chlorophylls,
  viii) cerium (Ce),
  ix) rhenium (Re),
  x) titanium (Ti),
  xi) silicon (Si),
  xii) tin oxides,
  xiii) zirconium (Zr),
  xiv) niobium (Nb),
  xv) indium (In),
  xvi) selenium (Se),
  xvii) aluminium oxides, and c) one or more basifying agent(s);

it being understood that the pH at the end of the method is alkaline, i.e. greater than 7 and preferably between 8 and 12, particularly between 8 and 10.5.

Another subject-matter of the invention relates to a cosmetic composition for the dyeing of keratinous fibres, comprising:

one or more ingredient(s) a) as defined above;
one or more ingredient(s) b) as defined above and
one or more ingredient(s) c) as defined above;

or a cosmetic composition as used in the dyeing method which comprises:

one or more ingredient(s) a) as defined above;
one or more gold derivative(s) as defined above;

it being understood that the pH of the compositions is greater than 7 and preferably between 8 and 12, particularly between 8 and 10.5.

Another subject-matter of the invention relates to a multi-compartment device comprising the ingredients a) to c) as defined above.

Another subject-matter of the invention relates to the use, for the dyeing of keratinous fibres, such as the hair, of the combination of a) to c) as defined above or of the combination a) as defined above and b) one or more gold derivative(s).

The method according to the invention exhibits the advantage of dyeing human keratinous fibres, with powerful, chromatic dyeing results which are resistant to washing operations, perspiration, sebum and light, and which are moreover long-lasting, without detrimental change to the said fibres. Furthermore, the colorations obtained starting from the method give uniform colours from the root to the end of a fibre (little coloration selectivity).

a) Ortho-Diphenol Derivative:

A particular form of the invention relates to ortho-diphenol derivatives or mixtures of compounds comprising at least one aromatic ring, preferably a benzene ring, comprising at least two hydroxyl (OH) groups carried by two adjacent carbon atoms of the aromatic ring which are not self-oxidizable derivatives comprising an indole unit. More particularly, they are different from 5,6-dihydroxyindole.

According to another specific embodiment of the invention, the ortho-diphenol derivative(s) are chosen from dihydroxyindoles and more particularly 5,6-dihydroxyindole.

The aromatic ring can more particularly be a fused aryl or fused heteroaromatic ring, i.e. optionally comprising one or more heteroatoms, such as benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline and isoquinoline, the said aromatic ring comprising at least two hydroxyl groups carried by two adjacent carbon atoms of the aromatic ring. Preferentially, the aromatic ring of the ortho-diphenol derivatives according to the invention is a benzene ring.

The term "fused ring" is understood to mean that at least two saturated or unsaturated and heterocyclic or non-heterocyclic rings exhibit a common bond, i.e. that at least one ring is placed side by side with another ring.

The ortho-diphenols according to the invention may or may not be salified. They may also be in aglycone form (without attached sugar) or in the form of glycosylated compounds.

More particularly, the ortho-diphenol derivative a) represents a compound of formula (I), or one of its oligomers, in salified or non-salified form:

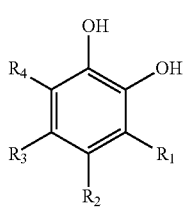
(I)

in which formula (I) the substituents:
$R_1$ to $R_4$, which are identical or different, represent:
  a hydrogen atom,
  a halogen atom,
  a hydroxyl radical,
  a carboxyl radical,
  an alkyl carboxylate or alkoxycarbonyl radical,
  an optionally substituted amino radical,
  an optionally substituted and linear or branched alkyl radical,
  an optionally substituted and linear or branched alkenyl radical,
  an optionally substituted cycloalkyl radical,
  an alkoxy radical,
  an alkoxyalkyl radical,
  an alkoxyaryl radical, it being possible for the aryl group to be optionally substituted,
  an aryl radical,
  a substituted aryl radical,
  a saturated or unsaturated heterocyclic radical, carrying or not carrying a cationic or anionic charge, optionally substituted and/or optionally fused with an aromatic ring, preferably a benzene ring, the said aromatic ring being optionally substituted, particularly by one or more hydroxyl or glycosyloxy groups,
  a radical comprising one or more silicon atoms,
  where two of the substituents carried by two adjacent carbon atoms $R_1$-$R_2$, $R_2$-$R_3$ or $R_3$-$R_4$ form, together with the carbon atoms carrying them, a saturated or unsaturated and aromatic or non-aromatic ring, optionally comprising one or more heteroatoms and optionally fused with one or more saturated or unsaturated rings optionally comprising one or more heteroatoms. In particular, $R_1$ to $R_4$ together form from one to four rings.

A specific embodiment of the invention relates to ortho-diphenol derivatives of formula (I), two adjacent substituents $R_1$-$R_2$, $R_2$-$R_3$ or $R_3$-$R_4$ of which cannot form, with the carbon atoms which carry them, a pyrrolyl radical. More particularly, $R_2$ and $R_3$ cannot form a pyrrolyl radical fused to the benzene ring carrying the two hydroxyl groups.

The saturated or unsaturated and optionally fused rings can also be optionally substituted.

The alkyl radicals are saturated and linear or branched hydrocarbon radicals, generally $C_1$-$C_{20}$ hydrocarbon radicals, particularly $C_1$-$C_{10}$ hydrocarbon radicals, preferably $C_1$-$C_6$ alkyl radicals, such as methyl, ethyl, propyl, butyl, pentyl and hexyl.

The alkenyl radicals are unsaturated and linear or branched $C_2$-$C_{20}$ hydrocarbon radicals, preferably comprising at least one double bond, such as ethylene, propylene, butylene, pentylene, 2-methylpropylene and decylene.

The aryl radicals are monocyclic or fused or non-fused polycyclic carbon-based radicals, preferentially comprising from 6 to 30 carbon atoms, at least one ring of which is aromatic; a phenyl, biphenyl, naphthyl, indenyl, anthracenyl and tetrahydronaphthyl are preferentially chosen from the aryl radical.

The alkoxy radicals are alkyloxy radicals with alkyl as defined above, preferably $C_1$-$C_{10}$ alkyloxy radicals, such as methoxy, ethoxy, propoxy and butoxy.

The alkoxyalkyl radicals are preferably $(C_1$-$C_{20})$alkoxy$(C_1$-$C_{20})$alkyl radicals, such as methoxymethyl, ethoxymethyl, methoxyethyl, ethoxyethyl, and the like.

The cycloalkyl radicals are generally $C_4$-$C_8$ cycloalkyl radicals, preferably cyclopentyl and cyclohexyl radicals. The cycloalkyl radicals can be substituted cycloalkyl radicals, in particular substituted by alkyl, alkoxy, carboxylic acid, hydroxyl, amine and ketone groups.

The alkyl or alkenyl radicals, when they are optionally substituted, can be substituted by at least one substituent carried by at least one carbon atom, chosen from:
  a halogen atom;
  a hydroxyl group;
  a $C_1$-$C_2$ alkoxy radical;
  a $C_1$-$C_{10}$ alkoxycarbonyl radical;
  a (poly)hydroxy$(C_2$-$C_4)$alkoxy radical;
  an amino radical;

a 5- or 6-membered heterocycloalkyl radical;

an optionally cationic 5- or 6-membered heteroaryl radical, preferentially an imidazolium radical, optionally substituted by a ($C_1$-$C_4$)alkyl radical, preferentially a methyl radical;

an amino radical substituted by one or two identical or different $C_1$-$C_6$ alkyl radicals, optionally carrying at least:
one hydroxyl group,
one amino group optionally substituted by one or two optionally substituted $C_1$-$C_3$ alkyl radicals, it being possible for the said alkyl radicals to form, with the nitrogen atom to which they are attached, a saturated or unsaturated and optionally substituted 5- to 7-membered heterocycle optionally comprising at least one other heteroatom identical to or different from nitrogen,
one quaternary ammonium group —$N^+R'R''R'''$ $M^-$ for which R', R" and R'", which are identical or different, represent a hydrogen atom or a $C_1$-$C_4$ alkyl group; and $M^-$ represents the counterion of the corresponding organic acid, inorganic acid or halide;
or one optionally cationic 5- or 6-membered heteroaryl radical, preferentially an imidazolium radical, optionally substituted by a ($C_1$-$C_4$)alkyl radical, preferentially a methyl radical;

an acylamino (—NR—COR') radical in which the R radical is a hydrogen atom or a $C_1$-$C_4$ alkyl radical optionally carrying at least one hydroxyl group and the R' radical is a $C_1$-$C_2$ alkyl radical; a carbamoyl (($R)_2$N—CO—) radical in which the R radicals, which are identical or different, represent a hydrogen atom or a $C_1$-$C_4$ alkyl radical optionally carrying at least one hydroxyl group; an alkylsulfonylamino (R'$SO_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl (($R)_2$N—$SO_2$—) radical in which the R radicals, which are identical or different, represent a hydrogen atom or a $C_1$-$C_4$ alkyl radical optionally carrying at least one hydroxyl group;

a carboxylic radical in the acid or salified form (preferably salified with an alkali metal or a substituted or unsubstituted ammonium);

a cyano group;

a nitro group;

a carboxyl or glycosylcarbonyl group;

a phenylcarbonyloxy group optionally substituted by one or more hydroxyl groups;

a glycosyloxy group; and a phenyl group optionally substituted by one or more hydroxyl groups.

The aryl or heterocyclic radicals or the aryl or heterocyclic part of the radicals, when they are optionally substituted, can be substituted by at least one substituent carried by at least one carbon atom chosen from:

a $C_1$-$C_{10}$ and preferably $C_1$-$C_8$ alkyl radical optionally substituted by one or more radicals chosen from the following radicals: hydroxyl, $C_1$-$C_2$ alkoxy, (poly)hydroxy($C_2$-$C_4$)alkoxy, acylamino, amino substituted by two identical or different $C_1$-$C_4$ alkyl radicals, optionally carrying at least one hydroxyl group, or it being possible for the two radicals to form, with the nitrogen atom to which they are attached, a saturated and optionally substituted 5- to 7-membered and preferably 5- or 6-membered heterocycle optionally comprising another heteroatom identical to or different from nitrogen;

a halogen atom;

a hydroxyl group;

a $C_1$-$C_2$ alkoxy radical;

a $C_1$-$C_{10}$ alkoxycarbonyl radical;

a (poly)hydroxy($C_2$-$C_4$)alkoxy radical;

an amino radical;

a 5- or 6-membered heterocycloalkyl radical;

an optionally cationic 5- or 6-membered heteroaryl radical, preferentially an imidazolium radical, optionally substituted by a ($C_1$-$C_4$)alkyl radical, preferentially a methyl radical;

an amino radical substituted by one or two identical or different $C_1$-$C_6$ alkyl radicals, optionally carrying at least:
one hydroxyl group,
one amino group optionally substituted by one or two optionally substituted $C_1$-$C_3$ alkyl radicals, it being possible for the said alkyl radicals to form, with the nitrogen atom to which they are attached, a saturated or unsaturated and optionally substituted 5- to 7-membered heterocycle optionally comprising at least one other heteroatom identical to or different from nitrogen,
one quaternary ammonium group —$N^+R'R''R'''$ $M^-$ for which R', R" and R'", which are identical or different, represent a hydrogen atom or a $C_1$-$C_4$ alkyl group; and $M^-$ represents the counterion of the corresponding organic acid, inorganic acid or halide;
or one optionally cationic 5- or 6-membered heteroaryl radical, preferentially an imidazolium radical, optionally substituted by a ($C_1$-$C_4$)alkyl radical, preferentially a methyl radical;

an acylamino (—NR—COR') radical in which the R radical is a hydrogen atom or a $C_1$-$C_4$ alkyl radical optionally carrying at least one hydroxyl group and the R' radical is a $C_1$-$C_2$ alkyl radical; a carbamoyl (($R)_2$N—CO—) radical in which the R radicals, which are identical or different, represent a hydrogen atom or a $C_1$-$C_4$ alkyl radical optionally carrying at least one hydroxyl group; an alkylsulfonylamino (R'$SO_2$—NR—) radical in which the R radical represents a hydrogen atom or a $C_1$-$C_4$ alkyl radical optionally carrying at least one hydroxyl group and the R' radical represents a $C_1$-$C_4$ alkyl radical or a phenyl radical; or an aminosulfonyl (($R)_2$N—$SO_2$—) radical in which the R radicals, which are identical or different, represent a hydrogen atom or a $C_1$-$C_4$ alkyl radical optionally carrying at least one hydroxyl group;

a carboxylic radical in the acid or salified form (preferably salified with an alkali metal or a substituted or unsubstituted ammonium);

a cyano group;

a nitro group;

a polyhaloalkyl group, preferentially trifluoromethyl;

a carboxyl or glycosylcarbonyl group;

a phenylcarbonyloxy group optionally substituted by one or more hydroxyl groups;

a glycosyloxy group; and a phenyl group optionally substituted by one or more hydroxyl groups.

The term "glycosyl radical" is understood to mean a radical resulting from a monosaccharide or polysaccharide.

The radicals comprising one or more silicon atoms are preferably polydimethylsiloxane, polydiphenylsiloxane, polydimethylphenylsiloxane or stearoxy dimethicone radicals.

The heterocyclic radicals are generally radicals comprising, in at least one ring, one or more heteroatoms chosen from O, N and S, preferably O or N, optionally substituted by in particular one or more alkyl, alkoxy, carboxylic acid, hydroxyl, amine or ketone groups. These rings can comprise one or more oxo groups on the carbon atoms of the heterocycle.

Mention may be made, among the heterocyclic radicals which can be used, of the furyl, pyranyl, pyrrolyl, imidazolyl, pyrazolyl, pyridyl or thienyl groups.

More preferably, the heterocyclic groups are fused groups, such as benzofuranyl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular by one or more OH groups.

The ortho-diphenols of use in the method of the invention can be natural or synthetic. The natural ortho-diphenols include the compounds which can be present in nature and which are reproduced by chemical (semi)synthesis.

The salts of the ortho-diphenols of the invention can be salts of acids or of bases. The acids can be inorganic or organic. Preferably, the acid is hydrochloric acid, which results in chlorides.

The bases can be inorganic or organic. In particular, the bases are alkali metal hydroxides, such as sodium hydroxide, which results in sodium salts.

According to a specific embodiment of the invention, the composition comprises, as ingredient a), one or more synthetic ortho-diphenol derivative(s) which do not exist in nature.

According to another preferred embodiment of the invention, the method for dyeing keratinous fibres uses, as ingredient a), one or more natural ortho-diphenol derivative(s).

More particularly, the ortho-diphenols which can be used in the method of the invention according to a) are in particular:
flavanols, for instance catechin and epicatechin gallate,
flavonols, such as quercetin,
anthocyanidins, such as cyanidin, delphinidin or petunidin,
anthocyanins or anthocyans, such as myrtillin,
ortho-hydroxybenzoates, for example gallic acid salts,
flavones, such as luteolin,
hydroxystilbenes, for example 3, 3',4,5'-tetrahydroxystilbene, optionally oxylated (for example glucosylated),
3,4-dihydroxyphenylalanine and derivatives thereof,
2,3-dihydroxyphenylalanine and derivatives thereof,
4,5-dihydroxyphenylalanine and derivatives thereof,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
ortho-polyhydroxyquinones,
ortho-polyhydroxyxanthones,
1,2-dihydroxybenzene and derivatives thereof,
1,2,4-trihydroxybenzene and derivatives thereof,
1,2,3-trihydroxybenzene and derivatives thereof,
2,4,5-trihydroxytoluene and derivatives thereof,
proanthocyanidins and in particular the proanthocyanidins A1, A2, B1, B2, B3 and C1,
proanthocyanins,
tannic acid,
ellagic acid,
and the mixtures of the preceding compounds.

When the dye precursors exhibit D and L forms, both forms can be used in the compositions according to the invention, as can the racemates.

According to one embodiment, the natural ortho-diphenols are derived from extracts of animals, bacteria, fungi, algae or plants, used in their entirety or partially. In particular as regards plants, the extracts result from plants or plant parts, such as fruit, including citrus fruit, vegetables, trees or shrubs. Use may also be made of mixtures of these extracts, which are rich in ortho-diphenols as defined above.

Preferably, the natural ortho-diphenol(s) of the invention result from extracts of plants or of plant parts.

For the purposes of the invention, these said extracts will be put, in their entirety, into the same category as compound a).

The extracts are obtained by extraction of various plant parts, such as, for example, the root, the wood, the bark, the leaf, the flower, the fruit, the seed, the pod or the peel.

Mention may be made, among the extracts of plants, of extracts of tea leaves and of rose.

Mention may be made, among the extracts of fruit, of extracts of apple, extracts of grape (in particular of grape seed) or extracts of cocoa beans and/or pods.

Mention may be made, among the extracts of vegetables, of extracts of potato or of onion peel.

Mention may be made, among the extracts of tree wood, of extracts of pine bark or extracts of logwood.

Use may also be made of mixtures of plant extracts.

According to a specific embodiment of the invention, the ortho-diphenol derivative(s) are natural extracts, rich in ortho-diphenols. According to a preferred form, the ortho-diphenol derivative(s) are solely natural extracts.

The natural extracts according to the invention can be provided in the form of powders or liquids. Preferably, the extracts of the invention are provided in the form of powders.

According to the invention, the synthetic ortho-diphenol derivative(s), the natural ortho-diphenol derivative(s) and/or the natural extract(s) used as ingredient a) in one or more composition(s) of use in the method according to the invention preferably represent(s) from 0.001% to 20% by weight of the total weight of the composition(s) comprising the ortho-diphenol(s) or the extract(s).

As regards the pure ortho-diphenols, the content in the composition(s) comprising them is preferably between 0.001% and 5% by weight of each of these compositions.

As regards the extracts, the content in the composition(s) comprising the extracts per se is preferably between 0.5% and 20% by weight of each of these compositions.

b) Metal Derivative(s)

The method of the invention uses one or more metal derivative(s) b) which catalyse the oxidation by atmospheric oxygen. These derivatives are chosen from metal salts, metal complexes, metal oxides, metal oxoanions, hydrates and their supported forms for which the metals are i) Au; ii) Mo; iii) Ag; iv) W; v) V; vi) Ru; vii) Mg; viii) Ce; ix) Re; x) Ti; xi) Si; xii) Sn; xiii) Zr; xiv) Nb; xv) In; xvi) Se; and xvii) Al as defined above, it being possible in particular for these derivatives to represent neither Mg halide nor Sn halide nor Al halide nor Ag nitrate.

The term "metal salt" is understood to mean a compound other than alloys, i.e. the salt consists of a metal combined with certain nonmetallic elements.

The formation of the metal salts derives from oxidative attack. The metal is oxidized to give a cationic entity and then combines with an anionic entity to give a salt. This formation takes place by applying the redox principles and the redox reaction (chemical reaction during which an electron transfer takes place in which the atom which captures the electrons is known as the "oxidizing agent" and the atom which gives up the electrons is known as the "reducing agent"); or via chemical exchange reactions between one salt and another salt or an acid, in the presence or absence of atmospheric oxygen. These reactions are known to those skilled in the art.

Preferentially, the salts according to the invention are soluble in water at a proportion of at least 0.0001 g/l.

The metal salts according to the invention can be introduced in the solid form into the compositions or can originate from a mineral or thermal natural water which is rich in these ions, or alternatively from seawater (especially water from the Dead Sea). They can also originate from inorganic compounds, such as plant extracts comprising them (cf., for example, Patent Document FR 2 814 943).

The term "metal complex" or "coordination compounds" is understood to mean systems in which the metal ion, the central atom, is chemically bonded to one or more electron donors (ligands). A ligand comprising various coordinating groups (capable of coordinating with a metal) gives metal compounds corresponding to principles of a coordination sphere with a predetermined number of electrons (internal complexes or chelates)—see Ullmann's Encyclopedia of Industrial Chemistry, "*Metal complex dyes*", 2005, p. 1-42. More particularly, the term "metal complex" is understood to mean:

i) metal dyes or "metal-complex dyes", which are complexed dyes derived from azo, azomethine, hydrazono or formazan dyes (free, bidentate, tridentate, tetradentate), such as those described in Ullmann's Encyclopedia of Industrial Chemistry, "Metal complex dyes", 2005, p. 1-42, which preferentially comprise Cu and Mg;

ii) compounds of the "aza[18]annulene" type, also known as "(metallo)porphyrins" and "phthalocyanines", which contain 4 and 8 nitrogen atoms, respectively, included in the perimeter of the macrocycle—see the work "*Color Chemistry*", H. Zollinger, 3rd Ed., Wiley-VCH, 2003, chap. 5. Aza[18]annulenes, p. 123-160. The metal ion is then at the centre of the said macrocycle bonded by coordination with two hydrogen atoms to the nitrogen atoms of pyrroles, it also being possible for the metal to be stabilized by one or more bidentate or non-bidentate ligands; the metal ion preferentially being $Mg^{2+}$ or $Cu^{2+}$;

the metal complex is particularly:
a "metalloporphyrin", consisting of a backbone comprising 4 pyrrole groups which are connected at their a and a' positions via 4 methine groups and comprise 16 $sp^2$ hybridized atoms, complexing a metal such as Cu or Mg, or a "chlorine" (corresponding to a porphyrin in which an external C=C double bond of a pyrrole group has been reduced) complexed to a metal, preferentially $Mg^{2+}$, such as the chlorophyll chromophore: chlorophyllin;

iii) "phthalocyanines", which are tetraaza analogues of tetrabenzoporphyrins, such as Monastral Fast Blue B (C.I. Pigment Blue 15); Monastral Fast Blue G (C.I. Pigment Blue 16) (see "*Color Chemistry*", H. Zollinger, 3rd Ed., Wiley-VCH, 2003, chap. 5. Aza[18]annulenes, p. 140); the sulfonyl derivatives Sirius light Turquoise Blue G (C.I. Direct Blue 86, copper phthalocyanine tetrasulfonic acid) and "phthalocyanines" as described in Ullmann's Encyclopedia of Industrial Chemistry, "Phthalocyanines", 2005, p. 1-34, which comprise Cu and Si.

The term "metal oxide(s)" is understood to mean the compounds of generic formula $A_xO_y$ with A representing a metal element and $1 \leq x \leq 4$ and $1 \leq y \leq 12$.

The term "metal oxoanion(s)" is understood to mean the compounds of generic formula $Z_zA_xO_y$ with A representing a metal element, Z representing an alkali metal, such as Li, Na or K, or a hydrogen atom or an ammonium ion, and $1 \leq z \leq 6$, $1 \leq x \leq 4$ and $1 \leq y \leq 12$.

The term "supported form(s)" is understood to mean the forms in which the metal derivative b) is impregnated onto a material known as a "support". The optional supports for these metal derivatives can be chosen from charcoal, silica, alumina, optionally charged polymers comprising counter-anions or counter-cations (counter-cation or counter-anion of the metal entity). By way of example, the polymers can be polyethylene glycol (PEG) and polystyrene.

1) According to another embodiment of the invention, the metal derivative(s) can also be chosen from the following copper derivative(s):

i) copper (Cu) oxide(s) where the copper is of oxidation state I or II (Cu(I) or (II));

ii) copper metal complexes, such as Cu(I) and (II) metalloporphyrin(s), and copper phthalocyanines and chlorophyllins;

iii) Cu(I) and (II) salt(s) chosen from:
a) Cu(II) halides of formula $CuHal(R^2)$ with Hal representing a halogen atom and $R^2$ representing a hydroxyl, ($C_1$-$C_6$)alkoxy or $R^1$—C(O)O— group, with $R^1$ representing a ($C_1$-$C_6$)alkyl group,
b) Cu(II) ($C_1$-$C_{16}$)alkylcarboxylates, such as Cu acetate,
c) Cu(($C_1$-$C_{16}$)alkyl)sulfates, such as ammoniacal Cu lauryl sulfate,
d) Cu (bi)carbonates, such as Cu carbonate,
e) Cu(II) ($C_1$-$C_{16}$)alkylpolycarboxylates, such as Cu citrate $Cu_3(C_6H_5O_7)_2$ or Cu succinate,
f) Cu(II) ($C_1$-$C_{16}$)alkylpolycarboxylates with the alkyl group optionally interrupted by one or more heteroatoms, such as the nitrogen atom, for example Cu edetate,
g) Cu(II) (poly)hydroxy($C_1$-$C_{16}$)alkylcarboxylates, such as Cu gluconate, Cu glycocholate or Cu lactate,
h) heterocycloalkylcarboxylates, such as Cu pidolate,
i) Cu deoxyribonucleate,
j) Cu oxalate,
k) Cu[(poly)($C_1$-$C_{16}$)alkyl]poly)phosphates, such as Cu diphosphate;

iv) metal complexes of Cu(I) or (II) comprising ligands, particularly those having mono-, di-, tri- or tetrafunctionalized ligands, such as:
a) Cu(II) complexes having a bisazomethine ligand of formula (α) below:

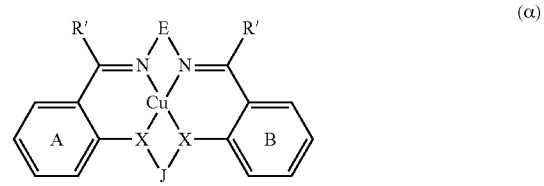

and also the hydrates thereof, in which formula (α):
E represents a linear or branched divalent ($C_1$-$C_6$) alkylene chain optionally substituted by oxo or linear or branched ($C_2$-$C_6$)alkylene groups,
either J is present and represents a group as defined for E and, in this case, X represents a heteroatom chosen from N and P;

or J is absent and X represents a heteroatom, such as O, S, N(R') or P(R'), with R' representing a hydrogen atom or a linear or branched $(C_1-C_6)$alkyl group, A and B, which are identical or different, are optionally substituted aryl groups or optionally substituted heteroaryl groups; and R' is as defined for N(R') and P(R');

b) Cu(II) complexes having an azomethine ligand, such as those of formula (β) below:

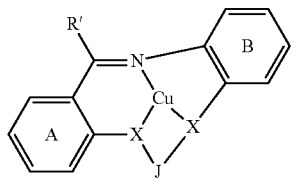

(β)

and also the hydrates thereof, in which formula (β): X, J, A, B, R' and J are as defined above in the formula (α);

c) azo direct dye derivatives having a copper complex, such as those of formula (γ) below:

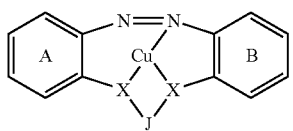

(γ)

with X, J, A and B as defined above in the formula (α);

d) the Cu(II) complexes resulting from dyes are in particular the Cu complexes of: 2,2'-dihydroxyazo; 2,2'-hydroxyaminoazo; 2,2'-dihydroxyazomethine, 2,2'-dihydroxycarboxyazo; 2,2'-dihydroxycarboxyazomethine; tridentate ligands derived from formazans, more particularly:

i) copper (Cu) oxide(s) where the copper is of oxidation state I or II (Cu(I) or (II)), ii) copper metal complexes, such as Cu(I) and (II) metalloporphyrins, copper phthalocyanines, as described in U.S. Pat. No. 3,931,249, and copper chlorophyllins, iii) Cu(I) and (II) salts chosen from:
a) Cu(II) halides of formula CuHal($R^2$) with Hal representing a halogen atom and $R^2$ representing a hydroxyl, $(C_1-C_6)$alkoxy or $R^1$—C(O)O— group, with $R^1$ as defined above,
b) Cu(II) $(C_1-C_{16})$alkylcarboxylates, such as Cu acetate,
c) Cu $((C_1-C_{16})$alkyl)sulfates, such as ammoniacal Cu lauryl sulfate,
d) Cu (bi)carbonates, such as Cu carbonate,
e) Cu(II) $(C_1-C_{16})$alkylpolycarboxylates, such as Cu citrate $Cu_3(C_6H_5O_7)_2$ or Cu succinate,
f) Cu(II) $(C_1-C_{16})$alkylpolycarboxylates with the alkyl group optionally interrupted by one or more heteroatoms, such as the nitrogen atom, for example Cu edetate,
g) Cu(II) (poly)hydroxy$(C_1-C_{16})$alkylcarboxylates, such as Cu gluconate, Cu glycocholate or Cu lactate,
h) heterocycloalkylcarboxylates, such as Cu pidolate,
i) Cu deoxyribonucleate,
j) Cu oxalate,
k) Cu[(poly)$(C_1-C_{16})$alkyl]poly)phosphates, such as Cu diphosphate, iv) metal complexes of Cu(I) or (II) comprising ligands, such as the metal complex dyes described in *Ullmann's Encyclopedia*, 2005, Wiley-VCH Verlag GmbH & Co, KgA, Weinheim, 10.1002/14356007.a16_299, pp. 1-42, particularly those having mono-, di-, tri- or tetrafunctionalized ligands, such as:

a) Cu(II) complexes having a bisazomethine ligand, such as those of formula (α) below:

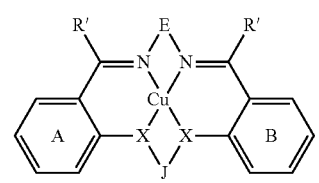

(α)

and also the hydrates thereof, in which formula (α):

E represents a linear or branched divalent $(C_1-C_6)$alkylene chain optionally substituted by oxo groups, or a linear or branched divalent $(C_2-C_6)$alkylene chain, such as ethylene —$CH_2$—$CH_2$—, a divalent arylene chain, such as ortho-phenylene, or a divalent heteroarylene chain, either J is present and represents a group as defined for E and, in this case, X represents a heteroatom chosen from N and P, or J is absent and X represents a heteroatom, such as O, S, N(R') or P(R'), with R' representing a hydrogen atom or a linear or branched $(C_1-C_6)$alkyl group, preferentially X=O, A and B, which are identical or different, particularly identical, are optionally substituted aryl groups or optionally substituted heteroaryl groups; preferentially, A and B are aryls, such as phenyl, and R' is as defined for N(R') and P(R'); preferentially, R' is a hydrogen atom;

more particularly, the Cu complex is such that X=O, E=ethylene, J is absent, R'=H, A and B=phenyl substituted in the para position with respect to the oxygen atom by an alkali metal sulfate group, such as sodium sulfate, or such as Brilliant Red [76683-16-4];

b) Cu(II) complexes having an azomethine ligand, such as those of formula (β) below:

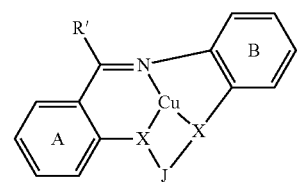

(β)

and also the hydrates thereof, in which formula (β): X, J, A, B and R' are as defined above in the formula (α); in particular, R' represents a hydrogen atom, B represents a phenyl, X represents an oxygen atom and A represents a phenyl optionally substituted in the para position with respect to the oxygen by a phenyl or a naphthyl, such as Pigment Yellow 117 [21405-81-2] and Pigment Yellow 129 [68859-61-0];
c) azo direct dye derivatives having a copper complex, such as those of formula (γ) below:

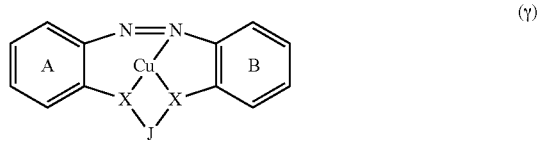

(γ)

with X, J, A and B as defined above in the formula (α); in particular, the compounds of formula (γ) are chosen from Acid Dyes, such as Sirius Light Blue 3 RL [13217-74-8], C.I. Direct Blue 93, Benzo Fast Red CGL, C.I. Direct Red 180, and those [92341-30-5], [119103-25-2], [116932-38-8], [113989-79-0];
bisazo direct dye derivatives carrying a copper complex, such as Direct Blue 80 [12222-003];
    formazan dye derivatives or formazan dyes as described in Ullmann's Encyclopedia, 2005, Wiley-VCH Verlag GmbH & Co, KgA, Weinheim, 10.1002/14356007.a16_299, p. 27, point 6 and 6.1.2: Bidentates, such as [53708-91-1], Tridentates or Tetradentates, such as [36090-18-3] and [109973-79];
d) the Cu(II) complexes resulting from dyes are in particular the Cu complexes of: 2,2'-dihydroxyazo; 2,2'-hydroxyaminoazo; 2,2'-dihydroxyazomethine, 2,2'-dihydroxycarboxyazo; 2,2'-dihydroxycarboxyazomethine; tridentate ligands derived from formazans.
According to a specific embodiment of the invention, the metal derivative(s) can be chosen from:
i) copper (Cu) oxide(s) where the copper is of oxidation state I or II (Cu(I) or (II)), more particularly where the Cu is of oxidation state I;
ii) copper metal complexes, such as Cu(I) and (II) metalloporphyrins, phthalocyanines, such as described above, and copper chlorophyllins a and b;

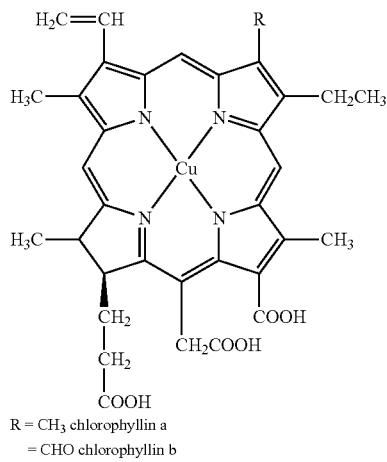

R = CH$_3$ chlorophyllin a
   = CHO chlorophyllin b and
iv) metal complexes of Cu(I) or (II) comprising ligands as defined above.
According to another specific embodiment of the invention, the copper metal derivative is chosen from copper gluconate, cupric chlorophyllin a or b, and CuHal(OH) with Hal representing a halogen atom, such as CuCl(OH).
i) According to a preferred embodiment of the invention, the metal derivative(s) is (are) of gold (Au), more particularly:
    a) gold(I) and (III) oxides, such as Au$_2$O$_3$,
    b) Au(I) and (III) hydroxides, such as Au(OH)$_3$, AuOH or Au(O)OH,
    c) gold(I) salts, particularly of formula AuHal with Hal representing a halogen atom (F, Cl, Br, I), such as AuCl or AuI,
    d) gold(III) salts chosen in particular from the following formulae:
        Au(Hal)$_3$ with Hal, which are identical or different, as defined above, such as AuCl$_3$ and AuBr$_3$,
        hydrated or non-hydrated ZAu(Hal)$_4$, with Z representing a hydrogen atom, an alkali metal, such as Li, Na or K, or an ammonium NH$_4^+$, and Hal, which are identical or different, as defined above, such as KAuCl$_4$ or HAuCl$_4$,
        Au(R)$_3$ with R, which are identical or different, representing:
            a (C$_1$-C$_6$)alkylcarbonyloxo group, where the alkyl group is linear or branched, such as methyl or tert-butyl, such as Au(OAc)$_3$,
            or alternatively one or two of the R groups represent a ligand L carrying at least one electron-donating group, such as amino, phosphino, hydroxyl or thiol, or the ligand is a "persistent" carbene, particularly of "Arduengo" type (imidazol-2-ylidenes); preferentially, the ligand is a phosphine, such as triphenylphosphine, for example (Ph$_3$P)AuOC(O)$^t$Bu,
    e) metal complexes of Au, such as Au(I) and (III) metalloporphyrins, gold(I) and (III) phthalocyanines or gold(I) and (III) chlorophyllins a or b.
Preferentially, the metal derivative(s) is (are) chosen from gold(I) and (III) oxides, such as Au$_2$O$_3$, gold hydroxides and gold(III) salts, such as ZAu(Hal)$_4$ and Au(R)$_3$. More preferentially, the metal derivative is chosen from oxides and hydroxides, such as Au$_2$O$_3$, Au(OH)$_3$ or AuOH.
ii) According to a specific embodiment of the invention, the metal derivative(s) is (are) of silver (Ag), more particularly:
    a) silver(I) and (II) oxides, such as Ag$_2$O and Ago;
    b) Ag(I) salts chosen in particular from the following formulae:
        AgHal, with Hal representing a halogen atom (F, Cl, Br, I), such as AgCl, AgBr or AgI;
        Ag$_x$R$^3{}_z$, with R$^3$, which are identical or different, representing:
            a sulfate group, such as Ag$_2$SO$_4$;
            a (C$_1$-C$_6$)alkylcarbonyloxo group, where the alkyl group is linear or branched and can optionally be substituted by a hydroxyl group, such as Ag acetate, Ag propionate or Ag lactate;
            x and z as defined above;
            with the exception of silver nitrate Ag(NO$_3$);
    c) Ag(I) metalloporphyrins;
    d) Ag(I) phthalocyanines as described in U.S. Pat. No. 3,931,249; and
    e) Ag(I) chlorophyllins a or b.
iii) According to a specific embodiment of the invention, the metal derivative(s) is (are) of molybdenum (Mo).
In particular, the metal derivative(s) of oxidation states (II) to (VI) is (are) as described in the *Kirk-Othmer Encyclopedia of Chemical Technology Copyright*© 2001, by John Wiley & Sons, Inc. Last updated: 17 Sep. 2009, "Molybdenum compounds", Edward I. Stieffel, pp. 871-895, or *Ullmann's Ency-* clopedia; WILEY-VCH Verlag GmbH & Co. KGaA, 2000-2005, "Molybdenum and Molybdenum Compounds".

More particularly:

a) Mo oxides, particularly Mo(VI) oxides, such as:
  molybdenum(VI) oxide, of formula $MoO_3$;

Mo(IV) oxides having β-diketone ligands $MoO_2L_2$ with the L ligands, which are identical or different, preferentially identical, representing a β-diketone of R—C(X)—C(R')—C(X)R" type with R and R", which are identical or different, representing a linear or branched $(C_1$-$C_6)$alkyl group, R' representing a hydrogen atom or a linear or branched $(C_1$-$C_6)$alkyl group and X representing an oxygen or sulfur atom or an N(R) group with R representing a hydrogen atom or a linear or branched $(C_1$-$C_6)$alkyl group; more particularly, the Mo dioxide is of formula $MoO_2[CH_3C(O)CHC(O)CH_3]_2$ [17524-05-9];

Mo(VI) oxide complexes originating from $MoO_3$ and from a $C_2$-$C_{10}$ hydroxycarboxylic acid ligand, especially citric acid or maleic acid, as described in the paper C. B. Knobler et al., *J. Chem. Soc. Dalton Trans.*, 1983, 1299, or from $C_2$-$C_{10}$ polyols comprising from 2 to 5 hydroxyl groups, in particular ethylene glycol or glycerol, as described in the paper F. A. Schroder and J. Scherle, Z. Naturforsch. B: *Anorg. Chem. Org. Chem.*, 28B (1973) 46; see also C. B. Knobler, B. R. Penfold and G. T. Wilkins, *J. Chem. Soc. Dalton Trans.*, 1980, 248;

the monohydrate $MoO_3.H_2O$ [39082-25-2], the dihydrate $MoO_3.2H_2O$ [25942-34-1] or molybdic acid $(H_2MoO_4.H_2O)$; molybdenum dioxide;

dihalodioxomolybdenum $(Hal)_2MoO_2$ with Hal, which are identical or different, as defined previously; in particular, Hal are identical and represent a chlorine atom;

molybdenum blues [66771-43-5], Mo oxide/Mo(VI) hydroxide and Mo(V) hydroxide mixture, as described in the paper V. K. Rudenko, *Koord. Khim.*, 5 (1979), 307; (*Sov. J. Coord. Chem.*, (*Engl. Transl.*), 5 (1979), 231); in particular $Mo^{6+}_3Mo^{5+}_3O_{18}H$, and the derivatives from condensation with phosphate ions;

mixtures of Mo oxides where the molybdenum has different valences Mo(VI)-Mo(V) (Mo oxide bronzes), as described in the paper M. Greenblat, *Chem. Rev.* 88, (1988) 31, more particularly, the binary bronzes and the tertiary bronzes $A_{0.33}MoO_3$ (A=Li, K, Rb, Cs, Tl); $A_{0.3}MoO_3$ (A=K, Rb, Tl); $A_{0.9}Mo_8O_{17}$ (A=Li, Na, K, Tl), and the rare earth metal bronzes $La_2Mo_2O_7$;

b) Mo oxoanions chosen from the molybdates $Z_2MoO_4$ with Z, which are identical or different, as defined previously, such as sodium molybdate $Na_2MoO_4$ or ammonium molybdate $(NH_4)_2MoO_4$;

c) polyoxometallates, such as: $[XY_uMo_{12-u}O_{40}]^{(3+u)-}(Z)_{(3+u)}$ with X and Y chosen from P, Si, V; $0 \leq u \leq 6$, and Z as defined above where Z represents a hydrogen atom; in particular, the polyoxometallate is of formula $H_5PV_2Mo_{10}O_{40}$;

d) binary Mo halides of oxidation states (II) to (VI), hexacoordinated with 6 halogens of Mo(V), (IV) and (III), the Mo atoms being bonded via halogen bonds, such as Mo(II) halide containing $[Mo_6Hal_8]^{4+}$ clusters bonded to halogen atoms to give $Mo_6Hal_{12}$ with Hal, which are identical or different, as defined above and more particularly Hal represents Cl;

e) molybdenum tetrahalides $(Hal)_4Mo$ with Hal, which are identical or different, as defined above, such as $MoCl_4$;

f) Mo sulfur derivatives chosen from:
  molybdenum disulfides [1317-33-5], molybdenum(IV) sulfides, $MoS_2$, the molybdates of formula $(Z)_2MoS_4$, with Z, which are identical or different, as defined above; in particular, Z represent an ammonium, such as tetrathiomolybdate $(NH_4)_2[MoS_4]$ [15060-55-6];

Mo sesquisulfides [12033-33-9]; dimolybdenum(III) trisulfides, $Mo_2S_3$;

tetrasulfide salts $Z\ MoS_{24}^-$ with Z as defined above, preferentially representing ammonium;

g) oxomolybdenum(VI) derivatives chosen from:
  $Mo(O)Hal_4$ with Hal, which are identical or different, being as defined above; in particular, Hal represents the F or Cl atom;

$Mo(O)_2Hal_2$ with Hal, which are identical or different, being as defined above; in particular, Hal represents the F, Cl and Br atom;

h) trihalooxomolybdenum(V) derivatives and these adducts with organic ligands L as defined above, L preferentially representing:

a bidentate group R—C(X)—CR'R"—C(X)—R'" with R and R'", which are identical or different, representing a linear or branched $(C_1$-$C_6)$alkyl group, R' and R", which are identical or different, representing a hydrogen atom or a linear or branched $(C_1$-$C_6)$alkyl group, R' and R" preferentially representing a hydrogen atom, and X representing an oxygen or sulfur atom or an N(R) group, with R representing a hydrogen atom or a linear or branched $(C_1$-$C_6)$alkyl group, such as acetylacetone;

a bidentate group of 2,2-bipyridyl type;

i) the oxomolybdenum derivative of formula $Mo(O)Hal_3.2$ L with L and Hal as defined above; preferentially, L represents an R"–O—R' with R and R' as defined above, such as diethyl ether, and a heteroaryl group, such as pyridine;

j) molybdates, isopolymolybdates and heteropolymolybdates comprising a tetrahedral anion $[MoO_4]^{2-}$, such as ammonium heptamolybdate (isopolymolybdate), $(NR'_4)_6Mo_7O_{24}$ hydrate, with R', which are identical or different, being as defined above; in particular, R' is a hydrogen atom;

k) molybdates of divalent cations, especially those which are water-soluble, such as the molybdates of $Mg^{2+}$, and molybdates of trivalent cations, especially of formula $A_2(MoO_4)_3$ or $A_2Mo_3O_{12}$, with A representing an atom chosen from Al, Cr, Bi and lanthanide;

l) heteropolymolybdates having an octahedron $[MoO_6]$ incorporating heteroatoms other than the oxygen atom, chosen especially from S, N and P; more specifically, the heteromolybdates are of formula $[X^+_nMo_{12}O_{40}])^{(8-n)-}$, comprising tetracoordinated heteroatoms (X), such as [12026-57-2], $H_3[PMo_{12}O_{40}]. 28H_2O$, m) Mo complexes with organosulfur ligands, such as phosphorodithioates or dithiophosphates and dithiocarbamates, $[Mo_2O_3L_4]$ and $[Mo_2O_2S_2L_2]$, with L as defined above; in particular, L represents $(RO)_2PS^-_2$ or $R_2NCS^-$ with R, which are identical or different, being as defined above;

n) molybdenum hexacarbonyl [13939-06-5], $Mo(CO)_6$;

o) organic pigments derived from alkali metal and alkaline earth metal molybdates, such as sodium molybdate derivatives, such as derivatives of i) diarylmethane (Auramine C.I. 655); ii) triarylmethane (Malachite Green C.I. 657, Brilliant Green C.I. 662; Rhoduline Blue 6G C.I. 658, Acronol Brilliant Blue C.I. 664, Methyl Violet B C.I. 680; Victoria Pure Blue BO C.I. Pr198); iii) xanthene (Rhodamine B C.I. 749, Rhodamine 6G); and p) Ca and Sr molybdates and q) Mo porphyrins, as described in the paper by T. Ma, K. Inoue, E. Abe, J. Yu, X. Wang and B. Zhang, *J. Electroanal. Chem.*, 537 (2002), 31, and Mo phthalocyanines, as described in U.S. Pat. No. 3,931,249.

Preferentially, the metal derivative is chosen from the compounds of formula $Z_2MoO_4$, such as $Na_2MoO_4$.

iv) According to a specific alternative form of the invention, the metal derivative(s) is (are) of tungsten (W), more particularly a) tungsten(VI) oxides, b) tungsten oxoanions, preferentially the hydrated or non-hydrated alkali metal tungstates $Z_2WO_4$, with Z, which are identical or different, as defined above, c) polyoxometallates, such as $[XY_uW_{12-u}O_{40}]^{(4+u)-}(Z)_{(4+u)}$, with X and Y chosen from P, Si or V and $0 \leq u \leq 6$; in particular, the polyoxometallate is of formula $H_4SiW_{12}O_{40}$.

Preferentially, the metal derivative is chosen from alkali metal tungstates, such as sodium tungstate $Na_2WO_4$.

v) According to a specific alternative form of the invention, the metal derivatives(s) is (are) of vanadium(V), more particularly a) vanadium oxides, such as $V_2O_5$, b) vanadium oxoanions chosen from vanadates and metavanadates, such as vanadium oxide acetylacetonate $VO(acac)_2$, $VOSO_4$ or ammonium vanadate, and c) polyoxometallates, such as $[XV_uM_{12-u}O_{40}]^{q-}(Z)_q$, with M=W or Mo, X=P or Si, $0 \leq u \leq 6$, q=3+x if M=Mo or q=4+x if M=W, and Z as defined above; in particular, the polyoxometallate is of formula $H_5PV_2Mo_{10}O_{40}$, and d) vanadium complexes, such as those described in U.S. Pat. No. 3,931,249. Preferentially, the metal derivative is chosen from those of formula $[XV_uMO_{12-u}O_{40}]^{(3+u)-}(Z)_{(3+u)}$ as defined above and in particular $H_5PV_2Mo_{10}O_{40}$.

vi) According to a specific embodiment of the invention, the metal derivatives(s) is (are) of ruthenium (Ru), more particularly i) ruthenium oxides, ii) ruthenium oxoanions, such as alkali metal perruthenate, and iii) ruthenium complexes, such as $(Hal)_2RuL_4$, with Hal, which are identical or different, as defined above and L, which are identical or different, being ligands as defined above.

Preferentially, the metal derivative is chosen from $RuCl_2(PPh_3)_4$, potassium perruthenate.

vii) According to a specific embodiment of the invention, the metal derivatives(s) is (are) of magnesium (Mg), particularly a) magnesium(II) oxide, b) magnesium(II) salts, such as magnesium(II) sulfate, c) magnesium(II) metalloporphyrins, d) magnesium(II) phthalocyanines, e) magnesium(II) chlorophyllins, f) magnesium(II) chlorophylls, metal complex dyes, as described in Ullmann's Encyclopedia, 2005, Wiley-VCH Verlag GmbH & Co, KgA, Weinheim, 10.1002114356007.a16_299, pp. 1-42, in particular those derived from formazans, as described in Ullmann's Encyclopedia, 2005, Wiley-VCH Verlag GmbH & Co, KgA, Weinheim, 10.1002/14356007.a16_299, p. 27, point 6.1.2.

Preferentially, the metal derivative is chosen from magnesium chlorophyllin a or b and magnesium chlorophyll a or b:

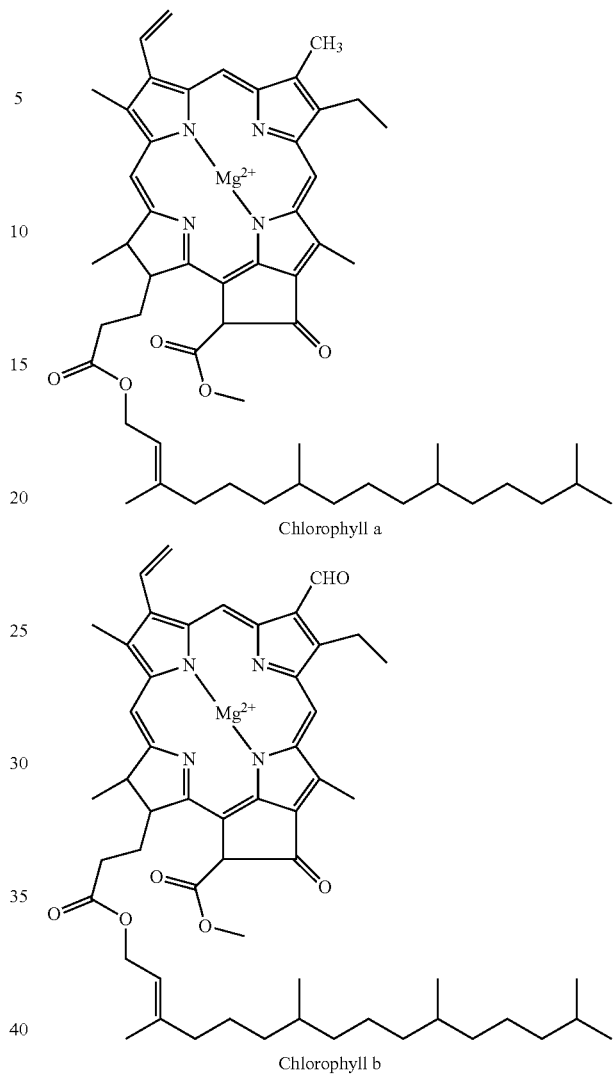

Chlorophyll a

Chlorophyll b viii) According to a specific embodiment of the invention, the metal derivatives(s) is (are) of cerium (Ce). In particular, the metal derivative(s) is (are) chosen from cerium oxides and their salts, their hydrates and their supported forms, such as cerium(IV) oxides and cerium(III) and (IV) salts. Mention may be made, by way of example, of Ce salts, oxides and hydroxides, such as those described in point 4.2 of Ullmann's Encyclopedia, "*Cerium Mischmetal, Cerium Alloys, and Cerium Compounds*", 2005, Wiley-VCH Verlag GmbH & Co. KGaA, Weinheim, 10.1002/14356007.a06 139, pp. 12. More particularly, the cerium oxide(s) is (are) chosen from cerium(IV) oxide hydrate [63394-44-5], [67285-52-3], cerium(III) rare earth metal oxide hydrates, or cerium(IV) oxide [1306-38-3], $CeO_2$. Preferentially, the metal oxide(s) is (are) cerium(IV) oxide $CeO_2$.

Preferentially, the metal derivative is chosen from cerium oxide $CeO_2$, cerium ammonium nitrate, cerium ammonium sulfate and cerium nitrate.

ix) According to a specific embodiment of the invention, the metal derivatives(s) is (are) of rhenium (Re), more particularly $R'ReO_3$, with R' representing a hydrogen atom or a linear or branched ($C_1$-$C_6$)alkyl group, such as $CH_3ReO_3$, or Re complexes, such as the phthalocyanines described, for example, in U.S. Pat. No. 3,931,249.

x) According to a specific embodiment of the invention, the metal derivatives(s) is (are) of titanium (Ti), particularly:
a) titanium(IV) salts, such as $Ti(SO_4)_2$,
b) titanium oxides, chosen in particular from titanium oxides and their salts, their hydrates and their supported forms. Mention may be made, by way of example, of Ti oxides and hydroxides, such as those described in Ullmann's Encyclopedia "*Titanium, Titanium Alloys, and Titanium Compounds*", 2005, Wiley-VCH Verlag GmbH & Co. KGaA, Weinheim, 10.1002114356007.a27 and 095, pp. 1-33. More particularly, the metal derivative(s) is (are) of titanium (Ti) and is (are) chosen from titanium(III) hydroxide and hydroxide $Ti(OH)_3$ and $TiO_3$, dititanium trioxide $Ti_2O_3$, alkaline earth metal titanium trioxides, alkaline earth metal titanium pentoxides, titanates of general formula $M^{II}TiO_4$, in which $M^{II}$ represents a metal Mg, Zn, Mn or Co, peroxytitanic acid and peroxytitanates $H_4TiO_5$, titanium(II) dioxide $TiO_2$ or titanium disulfide $TiS_2$. The oxides can originate from minerals, such as anatase and rutile, which comprise $TiO_2$; perovskite, which comprises calcium trioxide $CaTiO_3$; or sphene or titanite, which comprises $CaTi(SiO_4)O$;
c) Ti complexes, such as the phthalocyanines described, for example, in U.S. Pat. No. 3,931,249.

Preferentially, the metal derivative(s) is (are) $TiO_2$.

xi) According to a specific embodiment of the invention, the metal derivatives(s) is (are) of silicon (Si), more particularly silicon oxides and their salts, their hydrates and their supported forms, such as $SiO_2$.

xii) According to a specific embodiment of the invention, the metal derivatives(s) is (are) tin oxides and their salts, their hydrates and their supported forms. Mention may be made, by way of example, of tin oxides, such as those described in points 10 and 11 of *Ullmann's Encyclopedia "Tin, Tin Alloys, and Tin Compounds"*, 2005, Wiley-VCH Verlag GmbH & Co. KGaA, Weinheim, 10.1002/14356007.a27 049, pp. 27-29, particularly tin(II) oxide hydrate, such as $5SnO.2H_2O$ and tin(II) oxide, tin(IV) oxide hydrate $SnO_2.nH_2O$ and tin (IV) oxide $SnO_2$, alkali metal salts, such as sodium and potassium tin hydroxide of formula $M_2[Sn(OH)_6]$, with M representing an alkali metal, the tin hydroxides of formula $R_3SnOH$, $R_2SnOH_2$ or $RSnOH_3$, with R representing a hydrocarbon group, such as linear or branched ($C_1$-$C_6$)alkyl, or linear or branched ($C_1$-$C_6$)alkoxy, or (di) ($C_1$-$C_6$)alkylamino. Preferentially, the metal oxide(s) is (are) tin(IV) oxide $SnO_2$.

xiii) According to a specific embodiment of the invention, the metal derivatives(s) is (are) of zirconium (Zr).

In particular, the metal derivative(s) is (are) of zirconium (Zr) chosen from:
a) zirconium oxides and their salts, their hydrates and their supported forms. Mention may be made, by way of example, of Zr oxides and hydroxides, such as those described in points 2.2, 2.3 and 2.5 of Ullmann's Encyclopedia "*Zirconium and Zirconium Compounds*", 2005, Wiley-VCH Verlag GmbH & Co. KGaA, Weinheim, 10.1002/14356007.a28 543, pp. 15-18. More particularly, the zirconium oxide(s) is (are) chosen from zirconium oxide [1314-23-4], $ZrO_2$, zirconium oxide hydrate $[Zr_4(OH)_8.16H_2O]_8$, zirconium hydroxide dihalide, such as zirconium hydroxide dichloride [22196-48-1], and also the compounds of formula $Zr(OH)_2Hal_2.7H_2O$, with Hal representing a halogen atom, such as chlorine, zirconium oxyhalides, such as zirconium oxychloride, zirconium halide oxides, such as zirconium oxide dichloride, $ZrOCl_2.8H_2O$, $[Zr_4(OH)_8.16H_2O]Cl_8.12H_2O$, and zirconium monohalide, such as zirconium hydroxide monochloride $[Zr_4(OH)_{12}.16H_2O]Cl_4$;
b) and Zr complexes, such as the phthalocyanines described, for example, in U.S. Pat. No. 3,931,249.

Preferentially, the metal derivative(s) is (are) zirconium(II) oxide $ZrO_2$.

xiv) According to a specific embodiment of the invention, the metal derivatives(s) is (are) of niobium (Nb). In particular, the metal oxide(s) is (are) chosen from niobium oxides and their salts, their hydrates and their supported forms. Mention may be made, by way of example, of Nb oxides and hydroxides, such as those described in points 5.1 and 5.2 of Ullmann's Encyclopedia "*Niobium and Niobium Compounds*", 2005, Wiley-VCH Verlag GmbH & Co. KGaA, Weinheim, 10.1002/14356007.a17 251, pp. 5-6. More particularly, the Nb oxide(s) is (are) chosen from niobium pentoxide $Nb_2O_5$ [1313-96-8], alkali metal niobium trioxide, such as lithium niobium trioxide $LiNbO_3$ [12031-63-9] or $KNbO_3$ [12030-85-2], and niobium oxyhalides, such as niobium oxychloride [13597-20-1], $NbOCl_3$.

Preferentially, the metal derivative(s) is (are) niobium pentoxide $Nb_2O_5$.

xv) According to a specific embodiment of the invention, the metal derivative(s) is (are) of indium (In). In particular, the indium (In) derivative(s) is (are) chosen from indium oxides and their salts, their hydrates and their supported forms. Mention may be made, by way of example, of indium oxides, such as those described in point 7 of *Ullmann's Encyclopedia*, "Indium and Indium Compounds", 2005, Wiley-VCH Verlag GmbH & Co. KGaA, Weinheim, 10.1002/14356007.a14 157, pp. 7, more particularly indium(III) oxide of formula $In_2O_3$, indium(II) oxide [12136-26-4] of formula InO, indium(I) oxide [12030-22-7] of formula $In_2O$ and indium hydroxide [56108-30-6] of formula $In(OH)_3$, preferentially indium(III) oxide $In_2O_3$, preferentially $In_2O_3$.

xvi) According to a specific embodiment of the invention, the metal derivatives(s) is (are) of selenium (Se), more particularly $SeO_2$.

xvii) According to a specific embodiment of the invention, the metal derivatives(s) is (are) chosen from aluminium oxides and their salts, their hydrates and their supported forms. Mention may be made, by way of example, of aluminium oxides and hydroxides, such as those described in Ullmann's Encyclopedia "*Aluminium oxide*", 2005, Wiley-VCH Verlag GmbH & Co. KGaA, Weinheim, 10.1002/14356007.a06 139, pp. 1-40.

In particular, the aluminium hydroxide(s) and oxide(s) is (are) chosen from aluminium trihydroxide $Al(OH)_3$, aluminium oxide hydroxide AlO(OH), aluminium oxide $Al_2O_3$, hydrated or non-hydrated, and alkali metal aluminates, such as sodium aluminate $NaAlO_2$ [1302-42-7].

Preferentially, the metal oxide(s) is (are) aluminium oxide $Al_2O_3$.

A preferred embodiment of the invention relates to the ingredient b) which is in a sole metal entity chosen from i) to xvii) as defined above.

Preferentially, the metal derivative(s) b) is (are) chosen from metal salts, metal complexes, metal oxides, metal oxoanions, their supported forms, their hydrates and their mixtures for which the metal(s) is (are) chosen from i) gold (Au), ii) molybdenum (Mo), iv) tungsten (W), viii) cerium (Ce), xi) silicon (Si), xii) tin oxides, xiii) zirconium (Zr) and xv) indium (In).

More preferentially, the metal derivative(s) b) is (are) chosen from i) gold (Au), ii) silver (Ag), iii) molybdenum (Mo), iv) tungsten (W), v) vanadium (V), vi) ruthenium (Ru), vii)

magnesium (Mg) and xi) silicon (Si). In particular, the metal derivative(s) b) is (are) chosen from the compounds of formula $ZAu(Hal)_4$, such as $KAuCl_4$, $Au(R)_3Au_2O_3$; $Z_2MoO_4$; $Z_2WO_4$; $[XY_uMo_{12-u}O_{40}]^{q-}(Z)_q$ and $H_5(PV_2Mo_{10}O_{40})$, $(Hal)_2RuL_4$ as defined in the preceding claim; magnesium chlorophyllin; $KRuO_4$, $H_4SiW_{12}O_{40}$ and $Ag_2O$.

According to another alternative form, b) is chosen from the compounds of formula $ZAu(Hal)_4$; $Au(R)_3Au_2O_3$; $Z_2MoO_4$; $Z_2WO_4$; $[XY_xMo_{12-x}O_{40}]^{(3+x)-}(Z)_{(3+x)}$; $TiO_2$; $SiO_2$; $SnO_2$; $ZrO_2$ or $In_2O_3$.

According to a preferred embodiment of the invention, the metal derivative(s) b) is (are) of gold (Au). More particularly, the metal derivative(s) b) is (are) of gold (Au), with the exception of gold salts.

According to a preferred embodiment of the invention, the metal derivative(s) used represent from 0.0001% to 10% by weight approximately of the total weight of the composition (s) containing this or these metal salts, and more preferentially still from 0.0001% to 0.1% by weight approximately.

According to a preferred embodiment of the invention, the metal oxide(s), their salts, their hydrates and their supported forms used represent from 0.0001% to 10% by weight approximately of the total weight of the composition(s) containing this or these metal salts and more preferentially still from 0.0001% to 0.1% by weight approximately.

c) Basifying Agent(s)

The basifying agent used in the dyeing method according to the invention as third ingredient c) is an agent which makes it possible to increase the pH of the composition(s) in which it is present. The basifying agent is a Bronsted, Lowry or Lewis base. It can be inorganic or organic.

In particular, the said agent is chosen from i) (bi)carbonates, ii) aqueous ammonia, iii) alkanolamines, such as monoethanolamine, diethanolamine, triethanolamine and derivatives thereof, iv) oxyethylenated and/or oxypropylenated ethylenediamines, v) inorganic or organic hydroxides, vi) alkali metal silicates, such as sodium metasilicates, vii) amino acids, preferably basic amino acids, such as arginine, lysine, ornithine, citrulline and histidine, and viii) the compounds of following formula (II):

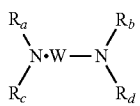

(II)

in which W is a divalent $(C_1-C_8)$alkylene radical optionally substituted by at least one hydroxyl group or at least one $(C_1-C_4)$alkyl radical and/or optionally interrupted by at least one heteroatom, such as oxygen or sulfur, or by an $—N(R_e)—$ group; and $R_a$, $R_b$, $R_b$, $R_d$ and $R_e$, which are identical or different, represent a hydrogen atom or a $(C_1-C_4)$alkyl or hydroxy$(C_1-C_4)$alkyl radical; preferentially, W represents a propylene radical.

The inorganic or organic hydroxides, particularly the inorganic or organic hydroxides, are preferably chosen from a) hydroxides of an alkali metal, b) hydroxides of an alkaline earth metal, such as sodium hydroxide or potassium hydroxide, c) hydroxides of a transition metal, such as hydroxides of metals from Groups III, IV, V and VI, d) hydroxides of lanthanides or actinides, quaternary ammonium hydroxides and guanidinium hydroxide.

The hydroxide can be formed in situ, such as, for example, guanidine hydroxide, by reacting calcium hydroxide and guanidine carbonate.

The term "(bi)carbonates i)" should be understood as meaning:
a) carbonates of alkali metals ($Met^+_2CO_3^{2-}$), of alkaline earth metals ($Met'^{2+}CO_3^{2-}$), of ammonium $((R''_4N^+)_2CO_3^{2-})$ or of phosphonium $((R''_4P^+)_2CO_3^{2-})$, with Met' representing an alkaline earth metal and Met representing an alkali metal, and R'', which are identical or different, representing a hydrogen atom or an optionally substituted $(C_1-C_6)$alkyl group, such as hydroxyethyl, and
b) bicarbonates, also known as hydrogencarbonates, of following formulae:
$R'^+HCO_3^-$, with R' representing a hydrogen atom, an alkali metal, an ammonium group $R''_4N^+$— or a phosphonium group $R''_4P^+$— where R'', which are identical or different, represent a hydrogen atom or an optionally substituted $(C_1-C_6)$alkyl group, such as hydroxyethyl, and, when R' represents a hydrogen atom, the hydrogencarbonate is then known as dihydrogencarbonate ($CO_2$, $H_2O$); and
$Met'^{2+}(HCO_3)_2$, with Met' representing an alkaline earth metal.

More particularly, the basifying agent is chosen from alkali metal or alkaline earth metal (bi)carbonates; preferentially alkali metal (bi)carbonates.

Mention may be made of Na, K, Mg and Ca carbonates or hydrogencarbonates and their mixtures, in particular of sodium hydrogencarbonate. These hydrogencarbonates can originate from a natural water, for example spring water from the Vichy basin or from La Roche-Posay or Badoit water (cf. patent, for example the document FR 2 814 943). In particular, mention may be made of sodium carbonate [497-19-8]= $Na_2CO_3$, sodium hydrogencarbonate or sodium bicarbonate [144-55-8]=$NaHCO_3$, and sodium dihydrogencarbonate=$Na(HCO_3)_2$.

According to a particularly advantageous embodiment, the basifying agent(s) c) is (are) chosen from alkanolamines and (bi)carbonates, in particular alkali metal or alkaline earth metal (bi)carbonates. Furthermore, they are preferentially found together during the dyeing method.

The basifying agent(s) as defined above preferably represent from 0.001% to 10% by weight of the weight of the composition(s) containing them, more particularly from 0.005% to 8% by weight of the composition.

The Chemical Oxidizing Agents:

In the context of the present invention, the method of the invention can be carried out in the absence of chemical oxidizing agent, that is to say by allowing atmospheric oxygen to act.

According to another dyeing method of the invention, the said method employs a chemical oxidizing agent.

The Term "Chemical Oxidizing Agent" is Understood to Mean:
a) ozone;
b) alkali metal or quaternary ammonium persalts, such as perborates, persulfates, percarbonates, peroxodiphosphates or Oxone®; the oxidizing agent is chosen in particular from sodium perborate, sodium persulfate, potassium persulfate, ammonium persulfate, sodium percarbonate and potassium percarbonate;
c) aliphatic $C_1-C_6$ and aromatic $C_6-C_{20}$ organic peracids and their percarboxylate forms, such as performic acid, peracetic acid, perbenzoic acid derivatives, pertrifluoroacetic acid or peroxyphthalic acid, peroxymaleic acid or peroxypropionic acid; the oxidizing agent is in particular peracetic acid;

d) organic peroxides, such as dioxirane, $C_1$-$C_6$ alkyl peroxides, benzoyl peroxide, peroxo($C_1$-$C_6$)alkyl carboxylates, bis(tri)($C_1$-$C_6$)alkylsilyl peroxides, such as bis(trimethylsilyl) peroxide, $C_1$-$C_6$ alkyl peroxydicarbonates and sodium nonanoyloxybenzenesulfonate, as described in the documents WO 1995000625 and U.S. Pat. No. 4,412,934;

e) oxidizing anions, such as nitrites, nitrates, hypochlorites, hypobromites, hypoiodites, chlorites, bromites, iodites, chlorates, bromates, iodates or periodates; the oxidizing agent is chosen in particular from an alkali metal hypochlorite or periodate, such as sodium hypochlorite or sodium periodate;

f) stable N-oxy (NO.) radicals, such as the 2,2,6,6-tetra($C_1$-$C_6$)alkylpiperidino-oxy radical, 2,2,6,6-tetra($C_1$-$C_6$) alkylmorpholino-oxy radical, Frémy nitrosodisulfonate salts or morpholine N-oxide; in particular, the oxidizing agent is chosen from the 2,2,6,6-tetramethylpiperidinyloxy radical;

g) hypervalent iodine derivatives, such as iodotriacetate, iodosobenzene, iodobenzenetriacetate, iodoperbenzoic acid derivatives, periodinanes, and alkyl and benzoyl hypoiodites; more preferentially, the oxidizing agent is chosen from iodotriacetate, iodosobenzene, iodobenzenetriacetate, iodoperbenzoic acid and Dess-Martin periodinane;

h) the following organic compounds: N-halosuccinimides, trichloroisocyanuric acid, N-hydroxyphthalimide and alkyl nitrites;

The optional supports for these oxidizing agents a) to h) can be chosen from silica, alumina, charcoal and charged or neutral polymers.

i) hydrogen peroxide or system(s) which generate hydrogen peroxide,
such as:
   i-1) urea hydrogen peroxide;
   i-2) polymeric complexes which can release hydrogen peroxide, such as polyvinylpyrrolidone/$H_2O_2$, in particular in the form of powders, and the other polymeric complexes described in U.S. Pat. No. 5,008,093, U.S. Pat. No. 3,376,110 and U.S. Pat. No. 5,183,901;
   i-3) oxidases which produce hydrogen peroxide in the presence of a suitable substrate (for example glucose in the case of glucose oxidase or uric acid with uricase);
   i-4) metal peroxides which generate hydrogen peroxide in water, such as calcium peroxide or magnesium peroxide;
   i-5) perborates; or
   i-6) percarbonates.

In particular, the chemical oxidizing agent(s) is (are) chosen from i) hydrogen peroxide or systems which generate hydrogen peroxide, more particularly $H_2O_2$.

According to a preferred embodiment of the invention, the method uses one or more system(s) which generate hydrogen peroxide chosen from i-1) urea hydrogen peroxide; i-2) polymeric complexes which can release hydrogen peroxide chosen from polyvinylpyrrolidone $H_2O_2$; i-3) oxidases; i-5) perborates and i-6) percarbonates.

Moreover, the composition(s) comprising hydrogen peroxide or generator(s) of hydrogen peroxide can also include various adjuvants conventionally used in hair dyeing compositions and as defined hereinbelow at the point entitled "cosmetic compositions".

According to a specific form of the invention, the hydrogen peroxide or the system(s) which generate(s) hydrogen peroxide used preferably represent(s) from 0.001% to 12% by weight, expressed as hydrogen peroxide, with respect to the total weight of the composition(s) containing it (them), and more preferentially still from 0.2% to 2.7% by weight.

The Photoirradiations by Electromagnetic Waves with Wavelengths within the UV Region Up to the IR Region:

The dyeing method according to the invention or the composition according to the invention can be employed or can be applied to keratinous fibres in the presence of one or more photoirradiation(s) by one or more electromagnetic wave(s) with a wavelength of between 10 nm in the ultraviolet (UV) region and 100 m in the infrared (IR) region. The term "photoirradiation with an electromagnetic wave" is understood to mean any exposure of the composition or part of the composition to a light wave during the hair dyeing method, it being possible for the light spectrum to comprise wavelengths within the UV region (10-400 nm), the visible region (400-750 nm) and the infrared region (745 nm to 100 μm).

According to a specific form of the invention, the dyeing method is carried out in natural sunlight or natural daylight.

According to another method for dyeing keratinous fibres, the source of the photoirradiation is artificial. Mention may be made, for the lamps emitting in the UV region, of those described in Ullmann's Encyclopedia "*Ultraviolet and Visible Spectroscopy*" 2008, Wiley-VCH Verlag GmbH & Co. KGaA, Weinheim, 10.1002/14356007.b05 383.pub2, point 3.2. Mention may be made, for the lamps in general, of those mentioned in Ullmann's Encyclopedia "*Lamps*" 2005, Wiley-VCH Verlag GmbH & Co. KGaA, Weinheim 10.1002/14356007.a15 115, and Ullmann's Encyclopedia "*Photochemistry*" 2005, Wiley-VCH Verlag GmbH & Co. KGaA, Weinheim 10.1002/14356007.a19 573, point 3.2 "light sources".

The lamps used in the method of the invention are in particular incandescent, halogen, fluorescent, mercury or low-pressure lamps, low-pressure lamps, for example sodium or neon lamps, high-pressure lamps, for example mercury lamps, halide lamps, flash lamps, for example xenon flash lamps, fluorescent excimer lamps, such as xenon fluorescent excimer lamps, Light Emitting Diodes or LEDs of 50 to 1000 mW, lamps emitting black light or Wood's light, and lasers. Preferentially, the artificial sources originate from mercury lamps, tungsten halogen lamps, white neon tubes or UV lamps emitting at 254 nm or at 365 nm.

The Water:

According to an embodiment of the invention, water is preferably included in the method of the invention. It can originate from the moistening of the keratinous fibres and/or from the composition(s) comprising the compounds a) to c) as defined above or from one or more other compositions. Preferably, the water originates at least from a composition comprising at least one compound chosen from a) to c) as defined above.

Cosmetic Compositions:

The cosmetic compositions according to the invention are cosmetically acceptable, i.e. they comprise a dyeing support which generally comprises water or a mixture of water and of one or more organic solvents or a mixture of organic solvents.

The term "organic solvent" is understood to mean an organic substance which is capable of dissolving or dispersing another substance without chemically modifying it.

Organic Solvents:

Mention may be made, as organic solvents, for example, of lower $C_1$-$C_4$ alkanols, such as ethanol and isopropanol, polyols and polyol ethers, such as 2-butoxyethanol, propylene glycol, propylene glycol monomethyl ether, diethylene glycol monoethyl ether, diethylene glycol monomethyl ether or hexylene glycol, and aromatic alcohols, such as benzyl alcohol or phenoxyethanol.

The organic solvents are present in proportions preferably of between 1% and 60% by weight approximately and more preferably still between 5% and 30% by weight approximately, with respect to the total weight of the dyeing composition.

Adjuvants:

The composition(s) of the dyeing method in accordance with the invention can also include various adjuvants conventionally used in hair dyeing compositions, such as anionic, cationic, nonionic, amphoteric or zwitterionic surfactants or their mixtures, anionic, cationic, nonionic, amphoteric or zwitterionic polymers or their mixtures, inorganic or organic thickening agents, in particular anionic, cationic, nonionic and amphoteric polymeric associative thickeners, antioxidants, penetrating agents, sequestering agents, fragrances, buffers, dispersing agents, conditioning agents, such as, for example, volatile or non-volatile and modified or unmodified silicones, film-forming agents, ceramides, preservatives and opacifying agents.

The said adjuvants are preferably chosen from surfactants, such as anionic or nonionic surfactants or their mixtures, and inorganic or organic thickening agents.

The above adjuvants are generally present in an amount for each of them of between 0.01% and 40% by weight, with respect to the weight of the composition, and preferably between 0.1% and 20% by weight, with respect to the weight of the composition.

Of course, a person skilled in the art will take care to choose this or these optional additional compound(s) so that the advantageous properties intrinsically attached to the composition(s) of use in the dyeing method in accordance with the invention are not, or not substantially, detrimentally affected by the envisioned addition(s).

The Additional Dyes:

The method employing the ingredients a) to c) as defined above and optionally one or more chemical oxidizing agent (s), water; or the cosmetic composition according to the invention comprising the ingredients a) to c) as defined above and optionally one or more chemical oxidizing agent(s), water can additionally employ or comprise one or more additional direct dyes.

These direct dyes are chosen, for example, from those conventionally used in direct dyeing, among which mention may be made of any commonly used aromatic and/or non-aromatic dye, such as neutral, acidic or cationic nitrobenzene direct dyes, neutral, acidic or cationic azo direct dyes other than "metal complex dyes", natural direct dyes other than ortho-diphenols, neutral, acidic or cationic quinone and in particular anthraquinone direct dyes, azine, triarylmethane or indoamine direct dyes, methines, styryls, porphyrins, metalloporphyrins, phthalocyanines, methine cyanines and fluorescent dyes. All these additional dyes are other than the ortho-diphenol derivatives according to the invention and the "metal complex dyes" or the porphyrins, metalloporphyrins and phthalocyanines belonging to a) according to the invention.

Mention may be made, among natural direct dyes, of lawsone, juglone, indigo, isatin, curcumin, spinulosin, apigenidin and orceins. Use may also be made of extracts or decoctions comprising these natural dyes and in particular henna-based cataplasms or extracts.

The additional direct dye(s) used in the composition(s) preferably represent from 0.001% to 10% by weight approximately of the total weight of the composition(s) comprising them and more preferentially still from 0.05% to 5% by weight approximately.

The method employing the ingredients a) to c) as defined above and optionally hydrogen peroxide or system which generates hydrogen peroxide, and water, or the cosmetic composition according to the invention comprising the ingredients a) to c) as defined above and optionally hydrogen peroxide or system which generates hydrogen peroxide, and water, can also employ or comprise one or more oxidation bases and/or one or more couplers conventionally used for the dyeing of keratinous fibres.

Mention may be made, among the oxidation bases, of para-phenylenediamines, bis(phenyl)alkylenediamines, para-aminophenols, bis-para-aminophenols, ortho-aminophenols, heterocyclic bases and their addition salts.

Mention may in particular be made, among these couplers, of meta-phenylenediamines, meta-aminophenols, meta-diphenols, naphthalene couplers, heterocyclic couplers and their addition salts.

The oxidation base(s) present in the composition(s) are generally each present in an amount of between 0.001% and 10% by weight of the total weight of the corresponding composition(s).

The cosmetic composition(s) of the invention can be provided in various formulation forms, such as a powder, a lotion, a foam, a cream or a gel, or in any other form appropriate for dyeing keratinous fibres. They can also be packaged in a propellant-free pump-action spray or under pressure in an aerosol container in the presence of a propellant and can form a foam.

pH of the Composition(s)

The method according to the invention employs the ingredients a), b) and c), with the final pH which is basic or alkaline, i.e. greater than 7, preferably between 8 and 12, in particular between 8 and 10.5. It is the same for the compositions according to the invention, which are basic or alkaline and which exhibit a pH of greater than 7, preferably between 8 and 12, in particular between 8 and 10.5.

The pH of these compositions can be adjusted to the desired value by means of basifying agents as defined above in c) or of acidifying agents usually used in the dyeing of keratinous fibres, or alternatively using conventional buffer systems.

Among the acidifying agents for the compositions used in the invention, examples that may be mentioned include inorganic or organic acids, for instance hydrochloric acid, orthophosphoric acid, sulfuric acid, carboxylic acids, for instance acetic acid, tartaric acid, citric acid or lactic acid, or sulfonic acids.

Among the basifying agents, they are agents as defined above in "c) basifyind agent(s)".

Dyeing Method in One or More Stages

According to a specific embodiment of the invention, the dyeing method is carried out, in one or more stages, by application, to the keratinous fibres, of one or more cosmetic compositions comprising, taken together or separately in the said composition(s), the following ingredients:

a) one or more ortho-diphenol derivative(s) as defined above;

b) one or more metal derivative(s) as defined above;

c) one or more basifying agent(s) as defined above;

it being understood that the pH at the end of the method is alkaline, i.e. that the pH of the composition comprising the ingredient c) is alkaline, i.e. greater than 7, preferably between 8 and 12, particularly between 8 and 10.5.

The leave-in time between the stages of application of the compositions comprising the ingredient(s) a), b) and/or c) is set at between 3 and 120 minutes, preferentially between 10 and 60 minutes and more particularly between 15 and 45 minutes.

The keratinous fibres may or may not be moistened beforehand.

More particularly, in the method of the invention, the compound(s) c) is (are) found either as a mixture with a) and b); or applied separately after application of a cosmetic composition comprising the ingredients a) and b); or else applied together with the ingredient a) after application of a cosmetic composition comprising the ingredient(s) b).

A specific embodiment of the invention relates to the methods for dyeing in one or two stages.

According to a specific embodiment of the invention, the method for dyeing keratinous fibres is carried out in two stages.

In an alternative form of the method in two stages, the first stage consists in applying, to the said fibres, a cosmetic composition comprising the ingredients a) and b) as defined above and then, in a second stage, a cosmetic composition comprising the ingredient c) as defined above is applied to the said fibres, it being understood that at least one of the two cosmetic compositions is aqueous.

According to a particularly advantageous method of the invention, the ingredient c) which is applied to the fibres comprises at least one (bi)carbonate as defined above. More particularly, the (bi)carbonate is in a composition in the presence of another alkaline agent, particularly an alkanolamine, such as monoethanolamine.

Preferentially, the dyeing method according to the invention is carried out in two stages, the first stage of which is to apply to the keratinous fibres the ingredients a) and b) together, then, in a second stage, to apply together the ingredients c), optionally then followed by post-treatment stages, such as the rinsing, for example with water, the shampooing with a conventional shampoo and/or the drying of the keratinous fibres.

For the latter methods, the leave-in time after application of the cosmetic composition for the first stage is generally set at between 3 and 120 minutes, preferentially between 10 and 60 minutes and more preferentially between 15 and 45 minutes. The leave-in time after application of the second cosmetic composition for the second stage is generally set at between 3 and 120 minutes, preferentially between 3 and 60 minutes and more preferentially between 5 and 30 minutes.

Whatever the form of application, the application temperature is generally between ambient temperature (15° C. to 25° C.) and 80° C. and more particularly between 15° C. and 45° C. Thus, after application of the composition according to the invention, the head of hair can advantageously be subjected to a heat treatment by heating to a temperature of between 30° C. and 60° C. In practice, this operation can be carried out using a styling hood, a hairdryer, an infrared ray dispenser and other conventional heating appliances.

Use may be made, both as means for heating and for smoothing the head of hair, of a heating iron at a temperature of between 60° C. and 220° C. and preferably between 120° C. and 200° C.

A specific form of the invention relates to a dyeing method which is carried out at ambient temperature (25° C.).

In all the specific forms and alternative forms of the methods described above, the compositions mentioned are ready-for-use compositions which can result from the extemporaneous mixing of two or more compositions and in particular of compositions present in dyeing kits.

Dyeing Device or Kit:

Another subject-matter of the invention is a multicompartment dyeing device or kit. Advantageously, this kit comprises from 2 to 5 compartments comprising from 2 to 5 compositions in which the ingredients a) one or more ortho-diphenol derivative(s), b) one or more metal derivative(s) and c) one or more basifying agent(s) are distributed, and optionally one compartment comprises hydrogen peroxide or one or more system(s) which generate(s) hydrogen peroxide and/or water, the said compositions comprising a), b) and/or c) being aqueous or pulverulent, with in particular at least one of these compositions being aqueous.

The compositions of the device according to the invention are packaged in separate compartments, optionally accompanied by suitable application means which are identical or different, such as fine brushes, coarse brushes or sponges.

The device mentioned above can also be equipped with a means which makes it possible to dispense the desired mixture on the hair, for example such as the devices described in Patent FR 2 586 913.

DYEING EXAMPLES

A) Colorimetric Results

The coloration of the hair is evaluated visually and read on a Minolta spectrocolorimeter (CM3600d, illuminant D65, angle 10°, SCI values) for the L*, a*, b* colorimetric measurements.

In this L*, a*, b* system, L* represents the intensity of the colour, a* indicates the green/red colour axis and b* indicates the blue/yellow colour axis. The lower the value of L, the darker or more intense the colour. The higher the value of a*, the redder the shade and, the higher the value of b*, the yellower the shade.

The variation in coloration between the dyed locks of permanent-waved grey hair, untreated (control) and after treatment, are defined by ($\Delta E^*_{absorption}$) according to the following equation:

$$\Delta E^*_{absorption} = \sqrt{(L^*-L_o^*)^2+(a^*-a_o^*)^2+(b^*-b_o^*)^2}$$

In this equation, L*, a* and b* represent the values measured after dyeing permanent-waved hair comprising 90% white hairs and $L_o^*$, $a_o^*$ and $b_o^*$ represent the values measured for untreated permanent-waved hair comprising 90% white hairs.

The higher the value of ΔE, the greater the difference in colour between the control locks and the dyed locks.

Protocol A:

1. Phase of Treatment with Ortho-Diphenols/Extracts:
Composition for 100 g:
   32 g of water
   32 g of ethanol
   32 g of propylene glycol
   0.168 g of molecule or extract
   $1.37 \times 10^{-4}$ mol of metal derivative The treatment of the keratinous fibres is carried out by application with a bath ratio of 1 g of lock per 12 g of composition to permanent-waved hair comprising 90% white hairs. The leave-in time after application is 30 minutes in an oven at 50° C. under aluminium foil.

Phase of Development of the Colour:
Alkaline composition (pH 9.5) per 100 g
   2.6 g of ammonium bicarbonate
   2 g of monoethanolamine
   q.s. for 100 g of water The treatment of the keratinous fibres is subsequently carried out by application to the hair with a bath ratio of 1 g of hair per 2.5 g of developing composition. The leave-in time after application is 10 minutes at ambient temperature.

2. Rinsing, Shampooing and Drying

The treatment is terminated by rinsing with water, shampooing using a conventional shampoo and drying with a hairdryer.

Protocol B:

1. Phase of Treatment with Ortho-Diphenols/Extracts:

Composition for 100 g:
- 32 g of water
- 32 g of ethanol
- 32 g of propylene glycol
- 0.42 g of molecule or extract
- $1.37 \times 10^{-4}$ mol of metal additive The treatment of the keratinous fibres is carried out by application with a bath ratio of 1 g of lock per 12 g of composition to permanent-waved hair comprising 90% white hairs. The leave-in time after application is 30 minutes in an oven at 50° C. under aluminium foil.

2. Development Phase:

Alkaline composition (pH 9.5) per 100 g
- 2.6 g of ammonium bicarbonate
- 2 g of monoethanolamine
- q.s. for 100 g of water The treatment of the keratinous fibres is subsequently carried out by application to the hair with a bath ratio of 1 g of hair per 2.5 g of developing composition. The leave-in time after application is 10 minutes at ambient temperature.

3. Rinsing, Shampooing and Drying

The treatment is terminated by rinsing with water, shampooing using a conventional shampoo and drying with a hairdryer.

ΔE Results:

i) with, as ortho-diphenol ingredient a), quercetin:

| Examples | Metal derivative b) | Protocol | $\Delta E_{absorption}$ |
|---|---|---|---|
| 1 | $Na_2MoO_4$—$2H_2O$ | A | 23.1 |
| 2 | $TiO_2$ | A | 18.0 |
| 3 | $ZrO_2$ | A | 19.3 |
| 4 | $Au_2O_3$ | B | 21.8 |
| 5 | $Au(OH)_3$ | B | 22.4 |
| 6 | AuOH | B | 22.1 |
| 7 | $SnO_2$ | B | 24.3 |
| 8 | $In_2O_3$ | B | 23.0 |
| 9 | $SiO_2$ | B | 22.8 |
| 10 | $CeO_2$ | B | 23.0 | ii) with, as ortho-diphenol ingredient a), haematein:

| Examples | Metal derivative b) | Protocol | $\Delta E_{absorption}$ |
|---|---|---|---|
| 11 | $Au_2O_3$ | B | 22.4 |
| 12 | $Au(OH)_3$ | B | 23.7 |
| 13 | AuOH | B | 23.7 |
| 14 | $SnO_2$ | B | 25.0 |
| 15 | $In_2O_3$ | B | 25.7 |
| 16 | $SiO_2$ | B | 25.3 |
| 17 | $CeO_2$ | B | 21.7 | iii) with, as ortho-diphenol ingredient a), haematoxylin:

| Examples | Metal derivative b) | Protocol | $\Delta E_{absorption}$ |
|---|---|---|---|
| 18 | $KAuCl_4$ | B | 22.0 | iv) with, as ingredient a), an extract: onion extract:

| Examples | Metal derivative b) | Protocol | $\Delta E_{absorption}$ |
|---|---|---|---|
| 19 | $Na_2MoO_4$—$2H_2O$ | A | 18.0 |
| 20 | Sodium tungstate - $2H_2O$ | A | 19.0 |

From the above results of the tables, it is clearly apparent that the dyeing method and the composition according to the invention, comprising a) an ortho-diphenol and extract in combination with b) a metal derivative in c) an alkaline medium, make it possible to efficiently dye whether this is on keratinous fibres characterized in particular by a large difference in colour between the control locks before treatment (NW) and the dyed locks (high $\Delta E_{absorption}$).

B) Comparative Tests with Respect to EP 0 664 114

Comparative protocol described in EP 0 664 114 with 4-methylcatechol (0.8 mmol)+resorcinol (0.4 mmol)+sodium persulfate (0.8 mmol)+bicarbonate buffer+metal salt (0.025 mmol), according to Example 5 of EP 0 664 114 (p. 7 and 8):

The dyeing per pair of compositions was evaluated. The first composition corresponds to that of the state of the art under the same experimental conditions (Example 5 of EP 0 664 114) and the composition according to the invention differs from that of the state of the art only in the replacement of the copper salt (copper acetate) by the type of metal salt according to the invention (same number of moles as the comparative=0.025 mmol).

The treatment of the keratinous fibres is carried out by application with a bath ratio of 1 g of lock per 5 g of composition to sensitized hair with an alkaline sensitivity of 25.6 (AS 25.6). The leave-in time after application is 30 minutes at ambient temperature.

Colorimetric Results with Regard to the Chromaticity and Homogeneity:

The L, a and b values are measured by the Minolta spectrocolorimeter (CM3600d, illuminant D65, angle 10°, SCI values) for the L*, a*, b* colorimetric measurements.

Chromaticity: C*

The chromaticity in the CIE L*, a*, b* system is calculated according to the following equation:

$$C^* = \sqrt{a^{*2} + b^{*2}}$$

The higher the value of C*, the more chromatic the coloration obtained.

Homogeneity of the Coloration or Selectivity: $\Delta E^*_{select}$

The variation in coloration between the dyed locks of natural grey hair and the permanent-waved or sensitized locks (AS 25.6) is defined by ($\Delta E^*_{select}$) according to the following equation:

$$\Delta E^*_{select} = \sqrt{(L^* - L_o^*)^2 + (a^* - a_o^*)^2 + (b^* - b_o^*)^2}$$

In this equation, L*, a* and b* represent the values measured after dyeing permanent-waved or sensitized locks (AS 25.6)

comprising 90% white hairs and $L^*_0$, $a_0^*$ and $b_0^*$ represent the values measured for natural hair comprising 90% white hairs after dyeing.

The higher the value of ΔE, the more visible the difference in colour between the natural and permanent-waved or sensitized locks, thus reflecting the effect of coloration selectivity between the root and the end. The smaller the value of $\Delta E_{select}$, the less selective the coloration and the more homogeneous the colour. The term "unison" dyeing is also heard.

Case with Metal Salt: Ag
Result with Copper Acetate According to the State of the Art:
 on grey lock comprising 90% natural white hairs (90NW) L*a*b*: 44.48/10.17/28.85,
 $\Delta E^*_{absorption}$=23.6, chromaticity C*=30.6
 on AS 25.6 lock L*a*b*: 37.42/18.56/34.80
 $\Delta E^*_{absorption}$=13.7, chromaticity C*=39.4
Results with Silver $Ag_2O$: More Chromatic
 on 90NW lock L*a*b*: 46.15/8.73/33.80, $\Delta E^*_{absorption}$=25.6, chromaticity C*=34.9
 on AS 25.6 lock L*a*b*: 40.83/15.9/38.09, $\Delta E^*_{absorption}$=12.3, chromaticity C*=41.3
Homogeneity or Selectivity:
$\Delta E_{select}$=12.47 (state of the art)
$\Delta E_{select}$=9.90 ($Ag_2O$)
Case with Metal Salts: W and Si
Results with $H_4SiW_{12}O_{40}$: less selective vs. $\Delta E_{select}$=12.47 (state of the art)
 on 90NW lock L*a*b*: 49.76/6.04/23.14
 on AS 25.6 lock L*a*b*: 45.12/11.72/31.75
i.e. $\Delta E_{select}$=11.30 ($H_4SiW_{12}O_{40}$)
Case with Metal Salts: Au
Results with $KAuCl_4$: significantly less selective vs. $\Delta E_{select}$=12.47 (state of the art)
 on 90NW lock L*a*b*: 45.19/7.18/26.43
 on AS 25.6 lock L*a*b*: 43.07/14.02/33.16
i.e. $\Delta E_{select}$=9.8 ($KAuCl_4$)
Case with Mg
Results with magnesium chlorophyllin: significantly less selective vs. $\Delta E_{select}$=12.47 (state of the art)
 on 90NW lock L*a*b*: 47.96/5.61/27.68
 on AS 25.6 lock L*a*b*: 43.77/11.92/33.43
i.e. $\Delta E_{select}$=9.5
Case with Metal Salts: V and Mo
Results with $H_5(PV_2MO_{10}O_{40})$: significantly less selective vs. $\Delta E_{select}$=12.47 (state of the art)
 on 90NW lock L*a*b*: 46.42/4.85/20.65
 on AS 25.6 lock L*a*b*: 37.69/9.39/25.35
i.e. $\Delta E_{select}$=10.9 [$H_5(PV_2Mo_{10}O_{40})$]
Case with Metal Salts: Ru
Results with $KRuO_4$: significantly less selective vs. $\Delta E_{select}$=12.47 (state of the art)
 on 90NW lock L*a*b*: 46.18/8.12/28.17
 on AS 25.6 lock L*a*b*: 40.01/14.96/33.93
i.e. $\Delta E_{select}$=10.9 ($KRuO_4$)
Comparative Protocol with Another Type of Ortho-Diphenol: Quercetin+Bicarbonate+Metal Salt:
1. Phase of Treatment with Ortho-Diphenols/Extracts:
Composition for 100 g:
 q.s. for 100 g of water
 12.8 g of ethanol
 12.8 g of propylene glycol
 1 g of quercetin
 $3.3 \times 10^{-3}$ mol of metal derivative
The treatment of the keratinous fibres is carried out by application with a bath ratio of 5 g of composition per 1 g of lock to permanent-waved hair comprising 90% white hairs. The leave-in time after application is 30 minutes on a heating plate at 30° C. in an aluminium foil.

2. Phase of Development of the Colour:
Alkaline composition (pH 9.5) per 100 g:
 2.6 g of ammonium bicarbonate
 2 g of monoethanolamine
 q.s. for 100 g of water
The treatment of the keratinous fibres is subsequently carried out by application to the hair with a bath ratio of 2.5 g of developing composition per 1 g of hair. The leave-in time after application is 10 minutes at ambient temperature. Rinsing with water, then shampooing and drying.
Results with copper acetate according to the state of the art:
 on 90PW lock L*a*b*: 49.90/8.14/36.82, $\Delta E^*_{absorption}$=26.3, chromaticity C*=37.7
Results with molybdenum $Na_2MoO_4$: significantly more chromatic than the state of the art
 on 90PW lock L*a*b*: 44.86/15.88/41.36, $\Delta E^*_{absorption}$=34.3, chromaticity C*=44.3
It is thus apparent that the colorations obtained with the composition according to the invention or the method according to the invention comprising a metal salt other than that of the state of the art unexpectedly contribute a significantly stronger chromaticity, a lower coloration selectivity and/or a greater absorption of coloration than the state of the art.

The invention claimed is:

1. A method for dyeing keratinous fibers comprising applying to the keratinous fibers, in one or more stages, at least one cosmetic composition comprising, together or separately:
 (a) at least one ortho-diphenol derivative;
 (b) at least one metal derivative chosen from metal salts, metal complexes, metal oxides, metal oxoanions, their supported forms, their hydrates and their mixtures, wherein the metal is chosen from:
  i) gold (Au),
  ii) molybdenum (Mo),
  iii) silver (Ag)(I) and (II),
  iv) tungsten (W),
  v) vanadium (V),
  vi) ruthenium (Ru),
  vii) magnesium (Mg)(II),
  viii) cerium (Ce),
  ix) rhenium (Re),
  x) titanium (Ti),
  xi) silicon (Si),
  xii) tin (Sn),
  xiii) zirconium (Zr),
  xiv) niobium (Nb),
  xv) indium (In),
  xvi) selenium (Se), and
  xvii) aluminium (Al); and
 (c) at least one basifying agent;
wherein the pH of the composition comprising the at least one basifying agent is alkaline.

2. The method according to claim 1, wherein the at least one ortho-diphenol derivative is chosen from natural ortho-diphenol derivatives.

3. The method according to claim 1, wherein the at least one ortho-diphenol derivative is an ortho-diphenol comprising an aromatic ring chosen from benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline, isoquinoline and combinations thereof, said aromatic ring comprising at least two hydroxyl groups carried by two contiguous adjacent atoms of the aromatic ring.

4. The method according to claim 1, wherein the at least one ortho-diphenol derivative is chosen from compounds of formula (I) and its oligomers, in salified or non-salified form:

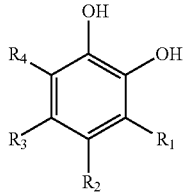

(I)

wherein:
R₁, R₂, R₃, and R₄, which may be identical or different, are chosen from:
hydrogen,
halogen atoms,
hydroxyl radicals,
carboxyl radicals,
alkyl carboxylates and alkoxycarbonyl radicals,
optionally substituted amino radicals,
optionally substituted, linear or branched alkyl radicals,
optionally substituted, linear or branched alkenyl radicals,
optionally substituted cycloalkyl radicals,
alkoxy radicals,
alkoxyalkyl radicals,
alkoxyaryl radicals, wherein the aryl group is optionally substituted,
aryl radicals,
substituted aryl radicals,
saturated or unsaturated heterocyclic radicals, optionally carrying a cationic or anionic charge, optionally substituted, and/or optionally fused with an optionally substituted aromatic ring, and
radicals comprising at least one silicon atom,
wherein two of the substituents carried by two adjacent carbon atoms R₁-R₂, R₂-R₃ or R₃-R₄ together form a saturated or unsaturated, aromatic or non-aromatic and substituted or unsubstituted ring, optionally comprising at least one heteroatom and optionally fused with one or more saturated or unsaturated and optionally substituted rings optionally comprising at least one heteroatom.

5. The method according to claim 4, wherein the ortho-diphenol derivative is chosen from:
flavonols,
anthocyanidins,
anthocyanins and anthocyans,
ortho-hydroxybenzoates,
flavones,
hydroxystilbenes,
3,4-dihydroxyphenylalanine and derivatives thereof,
2,3-dihydroxyphenylalanine and derivatives thereof,
4,5-dihydroxyphenylalanine and derivatives thereof,
dihydroxycinnamates,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
polyhydroxyquinones,
orthohydroxyxanthones,
1,2-dihydroxybenzene and derivatives thereof,
1,2,4-trihydroxybenzene and derivatives thereof,
1,2,3-trihydroxybenzene and derivatives thereof,
2,4,5-trihydroxytoluene and derivatives thereof,
proanthocyanidins,
proanthocyanins,
tannic acid,
ellagic acid,
and combinations thereof.

6. The method according to claim 2, wherein the natural ortho-diphenol derivatives are chosen from extracts of animals, bacteria, fungi, algae or plants.

7. The method according to claim 6, wherein the natural ortho-diphenol derivatives are chosen from:
extracts of tea leaves, extracts of rosemary leaves and extracts of mate leaves;
extracts of fruit;
extracts of vegetables; and
extracts of tree wood.

8. The method according to claim 1, wherein the at least one metal derivative is chosen from:
i) gold derivatives chosen from:
a) Au(I) and (III) oxides,
b) Au(I) and (III) hydroxides,
c) Au(I) and gold(III) salts, and
d) Au complexes;
ii) silver derivatives chosen from:
a) Ag(I) and (II) oxides,
b) Ag(I) and (II) salts,
c) Ag(I) metalloporphyrins,
d) Ag(I) phthalocyanines, and
e) Ag(I) chlorophyllins a or b;
iii) molybdenum derivatives chosen from:
a) Mo(VI) oxides,
b) Mo oxoanions,
c) polyoxometallates of formula: $[XY_uMo_{12-u}O_{40}]^{(3+u)-}(Z)_{(3+u)}$, wherein X and Y are independently chosen from P, Si, and V; $0 \leq u \leq 6$, and Z is chosen from hydrogen, alkali metals, and $NH_4^+$,
d) binary Mo halides of oxidation states (II) to (VI), hexacoordinated with 6 halogens of Mo(V), (IV) and (III), the Mo atoms being bonded via halogen bonds,
e) molybdenum tetrahalides (Hal)₄Mo, where Hal, which may be identical or different, are chosen from halogen atoms,
f) Mo sulfur derivatives,
g) oxomolybdenum(VI) derivatives,
h) trihalooxomolybdenum(V) derivatives and their adducts with organic ligands L carrying at least one electron-donating group,
i) the oxomolybdenum derivative of formula Mo(O)Hal₃.2L, wherein Hal is chosen from halogen atoms and L is a ligand carrying at least one electron-donating group,
j) molybdates, isopolymolybdates and heteropolymolybdates comprising a tetrahedral anion $[MoO_4]^{2-}$,
k) molybdates of divalent cations and trivalent cations,
l) heteropolymolybdates having an octahedron [MoO₆] incorporating heteroatoms other than the oxygen atom, chosen from S, N and P,
m) Mo complexes with organosulfur ligands,
n) molybdenum hexacarbonyl, Mo(CO)₆;
o) organic pigments derived from alkali metal and alkaline earth metal molybdates, and
p) Ca molybdates and Sr molybdates;
iv) tungsten derivatives chosen from:
a) tungsten(VI) oxides,
b) tungsten oxoanions, and c) polyoxometallates, $[XY_uW_{12-u}O_{40}]^{(4+u)-}(Z)_{(4+u)}$, wherein X and Y are independently chosen from P, Si and V, $0 \leq u \leq 6$, and Z is chosen from hydrogen, alkali metals, and $NH_4^+$;

v) vanadium derivatives chosen from:
  a) vanadium oxides,
  b) vanadium oxoanions, and
  c) polyoxometallates, $[XV_uM_{12-u}O_{40}]^{q-}(Z)_q$, wherein M is chosen from W and Mo, X is chosen from P and Si, $0 \leq u \leq 6$, q=3+x if M=Mo or q=4+x if M=W, and Z is chosen from hydrogen, alkali metals, and $NH_4^+$;

vi) ruthenium derivatives chosen from:
  a) ruthenium oxides,
  b) ruthenium oxoanions, and
  c) ruthenium complexes, $(Hal)_2RuL_4$, wherein Hal, which may be identical or different, are chosen from halogen atoms, and L, which may be identical or different, are chosen from ligands carrying at least one electron-donating group;

vii) magnesium metal derivatives chosen from:
  a) magnesium(II) oxide,
  b) magnesium(II) salts,
  c) magnesium(II) metalloporphyrins,
  d) magnesium(II) phthalocyanines,
  e) magnesium(II) chlorophyllins,
  f) magnesium(II) chlorophylls, and
  g) metal complex dyes;

viii) cerium derivatives chosen from cerium(IV) oxides and their salts, their hydrates and their supported forms and cerium(III) and (IV) salts;

ix) rhenium derivatives chosen from:
  a) $R'ReO_3$, wherein R' is chosen from hydrogen and linear or branched $(C_1-C_6)$alkyl groups, and
  b) rhenium complexes, x) titanium derivatives chosen from:
  a) titanium(IV) salts,
  b) titanium oxides and their salts, their hydrates and their supported forms, and
  c) titanium complexes;

xi) silicon derivatives chosen from silicon oxides;

xii) tin derivatives chosen from tin oxides and their salts, their hydrates and their supported forms;

xiii) zirconium derivatives chosen from:
  a) zirconium oxides and their salts, their hydrates and their supported forms, and
  b) zirconium complexes;

xiv) niobium derivatives chosen from niobium oxides and their salts, their hydrates and their supported forms;

xv) indium derivatives chosen from indium oxides and their salts, their hydrates and their supported forms;

xvi) selenium derivatives chosen from selenium oxides;

xvii) aluminum derivatives chosen from aluminium oxides and their salts, their hydrates and their supported forms; and xviii) combinations thereof.

9. The method according to claim 8, wherein the at least one metal derivative is chosen from:
i) gold derivatives chosen from:
  a) $Au_2O_3$,
  b) $Au(OH)_3$, AuOH, and Au(O)OH,
  c) AuHal, $Au(Hal)_3$, hydrated or non-hydrated $ZAu(Hal)_4$, and $Au(R)_3$, wherein Hal, which may be identical or different, are chosen from halogen atoms; Z is chosen from hydrogen, alkali metals, and $NH_4^+$; and R, which may be identical or different, are chosen from linear or branched $(C_1-C_6)$alkylcarbonyloxo groups, or one or two of the R groups are chosen from ligands L carrying at least one electron-donating group, and
  d) Au(I) and (III) metalloporphyrins, Au(I) and (III) phthalocyanines, and Au(I) and (III) chlorophyllins a or b;

ii) silver derivatives chosen from:
  a) $Ag_2O$ and AgO, and
  b) AgHal, wherein Hal is chosen from halogen atoms, and
  c) $Ag_xR^3_z$, wherein $R^3$, which may be identical or different, are chosen from sulfate groups and linear or branched $(C_1-C_6)$alkylcarbonyloxo groups optionally substituted with a hydroxyl group, $1 \leq z \leq 6$, and $1 \leq x \leq 4$;

iii) molybdenum derivatives chosen from:
  a) Mo oxides chosen from:
    Mo trioxide of formula $MoO_3$;
    Mo(IV) oxides having β-diketone ligands $MoO_2L_2$, wherein the L ligands, which may be identical or different, are chosen from β-diketones of R—C(X)—C(R')—C(X)R" type, with R and R", which may be identical or different, chosen from linear or branched $(C_1-C_6)$alkyl groups, R' is chosen from hydrogen and linear or branched $(C_1-C_6)$alkyl groups, and X is chosen from oxygen, sulfur, and N(R) groups, with R chosen from hydrogen and linear or branched $(C_1-C_6)$alkyl groups;
    Mo(VI) oxide complexes originating from $MoO_3$ and from a $C_2-C_{10}$ hydroxyalkylcarboxylic acid ligand or from $C_2C_{10}$ polyols comprising from 2 to 5 hydroxyl groups;
    the monohydrate $MoO_3.H_2O$, the dihydrate $MoO_3.2H_2O$, and molybdic acid $(H_2MoO_4.H_2O)$;
    molybdenum dioxide;
    dihalodioxomolybdenum $(Hal)_2MoO_2$, wherein Hal, which may be identical or different, are chosen from halogen atoms;
    molybdenum blues, Mo oxide/Mo(VI) hydroxide and Mo(V) hydroxide mixtures, and the derivatives from condensation of $Mo^{6+}_3Mo^{5+}_3O_{18}H$ with phosphate ions; and
    mixtures of Mo oxides wherein the molybdenum has different valences Mo(VI)-Mo(V) (Mo oxide bronzes),
  b) molybdates $Z_2MoO_4$, wherein Z, which may be identical or different, are chosen from hydrogen, alkali metals, and $NH_4^+$,
  c) polyoxometallates of formula: $[XY_uMo_{12-u}O_{40}]^{(3+u)-}(Z)_{(3+u)}$ wherein X and Y are independently chosen from P, Si, and V; $0 \leq u \leq 6$, and Z is chosen from hydrogen,
  d) Mo(II) halides containing $[Mo_6Hal_8]^{4+}$clusters bonded to halogen atoms to give $Mo_6Hal_{12}$, wherein Hal, which may be identical or different, chosen from halogen atoms,
  e) $MoCl_4$,
  f) Mo sulfur derivatives chosen from:
    molybdenum disulfides [1317-33-5], molybdenum (IV) sulfides, $MoS_2$, and molybdates of formula $(Z)_2MoS_4$, wherein Z, which may be identical or different, are chosen from hydrogen, alkali metals, and $NH_4^+$;
    Mo sesquisulfides; dimolybdenum(III) trisulfides, and $Mo_2S_3$; and
    tetrasulfide salts $ZMoS_{24}^-$, wherein Z is chosen from hydrogen, alkali metals, and $NH_4^+$, g) oxomolybdenum(VI) derivatives chosen from:
  Mo(O)Hal$_4$ wherein Hal, which may be identical or different, are chosen from halogen atoms; and
  Mo(O)$_2$Hal$_2$ wherein Hal, which may be identical or different, are chosen from halogen atoms,
h) trihalooxomolybdenum(V) derivatives and these adducts with organic ligands L chosen from:
  bidentate groups R—C(X)—CR'R"—C(X)—R''', wherein R and R''', which may be identical or different, are chosen from linear or branched (C$_1$-C$_6$) alkyl groups, R' and R", which may be identical or different, are chosen from hydrogen and linear or branched (C$_1$-C$_6$)alkyl groups, and X is chosen from oxygen, sulfur, and N(R) groups, with R chosen from hydrogen and linear or branched (C$_1$-C$_6$) alkyl groups; and
  bidentate groups of 2,2-bipyridyl type,
i) the oxomolybdenum derivative of formula Mo(O)Hal$_3$.2L, wherein Hal is chosen from halogen atoms and L is a ligand chosen from R"—O—R', with R' and R", which may be identical or different, chosen from hydrogen and linear or branched (C$_1$-C$_6$)alkyl groups,
j) ammonium heptamolybdate (isopolymolybdate) and (NR'$_4$)$_6$Mo$_7$O$_{24}$ hydrate, with R', which may be identical or different, chosen from hydrogen and linear or branched (C$_1$-C$_6$)alkyl groups,
k) molybdates of Mg$^{2+}$, A$_2$(MoO$_4$)$_3$, and A$_2$Mo$_3$O$_{12}$, wherein A is chosen from Al, Cr, Bi, and lanthanide,
l) heteropolymolybdates of formula [X$^+$$_n$Mo$_{12}$O$_{40}$]$^{(8-n)-}$, comprising tetracoordinated heteroatoms (X),
m) phosphorodithioates, dithiophosphates, dithiocarbamates, [Mo$_2$O$_3$L$_4$], and [Mo$_2$O$_2$S$_2$L$_2$], wherein L, which may be identical or different, are chosen from ligands carrying at least one electron-donating group,
n) sodium molybdate derivatives of diarylmethane; sodium molybdate derivatives of triarylmethane; and sodium molybdate derivatives of xanthenes;
iv) tungsten derivatives chosen from:
  a) hydrated or non-hydrated alkali metal tungstates Z$_2$WO$_4$, wherein Z, which may be identical or different, are chosen from hydrogen, alkali metals, and NH$_4$$^+$, and
  b) H$_4$SiW$_{12}$O$_{40}$ polyoxometallate;
v) vanadium derivatives chosen from:
  a) V$_2$O$_5$,
  b) vanadates and metavanadates, and
  c) H$_5$PV$_2$MO$_{10}$O$_{40}$;
vi) ruthenium derivatives chosen from:
  a) alkali metal perruthenates, and
  b) RuCl$_2$(PPh$_3$)$_4$;
vii) magnesium metal derivatives chosen from:
  a) magnesium(II) sulfate, and
  b) metal complex dyes derived from formazans;
viii) cerium derivatives chosen from cerium oxide CeO$_2$, cerium ammonium nitrate, cerium ammonium sulfate, and cerium nitrate;
ix) rhenium derivatives chosen from CH$_3$ReO$_3$ and phthalocyanines;
x) titanium derivatives chosen from:
  a) Ti(SO$_4$)$_2$,
  b) titanium(III) hydroxide Ti(OH)$_3$, TiO$_3$, dititanium trioxide Ti$_2$O$_3$, alkaline earth metal titanium trioxides, alkaline earth metal titanium pentoxides, titanates of general formula M$^{II}$TiO$_4$, wherein M$^{II}$ is chosen from Mg, Zn, Mn and Co, peroxytitanic acid, peroxytitanates H$_4$TiO$_5$, titanium(II) dioxide TiO$_2$, and titanium disulfide TiS$_2$, and
  c) phthalocyanines;
xi) silicon derivatives chosen from SiO$_2$; and
xii) tin derivatives chosen from tin(II) oxide hydrate 5SnO.2H$_2$O, tin(II) oxide, tin(IV) oxide hydrate SnO$_2$.nH$_2$O, tin(IV) oxide SnO$_2$, alkali metal salts of formula M$_2$[Sn(OH)$_6$], wherein M is chosen from alkali metals, tin hydroxides of formula R$_3$SnOH, R$_2$SnOH$_2$ or RSnOH$_3$, wherein R is chosen from linear or branched (C$_1$-C$_6$)alkyl groups, linear or branched (C$_1$-C$_6$)alkoxy groups, and (di) (C$_1$-C$_6$)alkylamino groups;
xiii) zirconium derivatives chosen from:
  a) zirconium oxide [1314-23-4], ZrO$_2$, zirconium oxide hydrate [Zr$_4$(OH)$_8$.16H$_2$O]$_8$, zirconium hydroxide dihalides, compounds of formula Zr(OH)$_2$Hal$_2$.7H$_2$O, wherein Hal, which may be identical or different, are chosen from halogen atoms, zirconium oxyhalides, zirconium halide oxides, ZrOCl$_2$.8H$_2$O, [Zr$_4$(OH)$_8$.16H$_2$O]Cl$_8$.12H$_2$O, and zirconium monohalides, and
  b) phthalocyanines;
xiv) niobium pentoxide Nb$_2$O$_5$ [1313-96-8], alkali metal niobium trioxides, and niobium oxyhalides;
xv) indium(III) oxide of formula In$_2$O$_3$, indium(II) oxide [12136-26-4] of formula InO, indium(I) oxide [12030-22-7] of formula In$_2$O, and indium hydroxide [56108-30-6] of formula In(OH)$_3$;
xvi) selenium derivatives chosen from SeO$_2$;
xvii) aluminium derivatives chosen from trihydroxide Al(OH)$_3$, aluminium oxide hydroxide AlO(OH), hydrated or nonhydrated aluminium oxide Al$_2$O$_3$, and alkali metal aluminates; and
xviii) combinations thereof.

10. The method according to claim 1, wherein the at least one metal derivative comprises at least one metal chosen from:
  i) gold (Au),
  ii) silver (Ag),
  iii) molybdenum (Mo),
  iv) tungsten (W),
  v) vanadium (V),
  vi) ruthenium (Ru),
  vii) magnesium (Mg), and
  xi) silicon (Si).

11. The method according to claim 1, wherein the at least one metal derivative is chosen from gold (Au) derivatives.

12. The method according to claim 1, wherein the at least one basifying agent is chosen from:
  i) (bi)carbonates,
  ii) aqueous ammonia,
  iii) alkanolamines and derivatives thereof,
  iv) oxyethylenated and/or oxypropylenated ethylenediamines,
  v) inorganic or organic hydroxides,
  vi) alkali metal silicates,
  vii) amino acids,
  viii) compounds of formula (II):

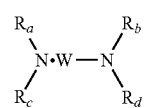

(II)

wherein W is chosen from divalent (C$_1$-C$_8$)alkylene radicals optionally substituted by at least one hydroxyl group or at least one (C$_1$-C$_4$)alkyl radical and/or optionally interrupted by at least one heteroatom, or by an —N(Re)— group; and $R_a$, $R_b$, $R_c$, $R_d$ and $R_e$, which may be identical or different, are chosen from hydrogen, ($C_1$-$C_4$)alkyl radicals, and hydroxy($C_1$-$C_4$)alkyl radicals, and ix) combinations thereof.

13. The method according to claim 1, wherein the at least one basifying agent is chosen from alkanolamines, alkali metal carbonates, alkaline earth metal carbonates, alkali metal bicarbonates, alkaline earth metal bicarbonates, and combinations thereof.

14. The method according to claim 1, wherein the method does not comprise the application of a chemical oxidizing agent other than atmospheric oxygen to the keratinous fibers.

15. The method according to claim 1, further comprising applying to the keratinous fibers at least one chemical oxidizing agent chosen from:

a) ozone;
b) alkali metal persalts and quaternary ammonium persalts;
c) aliphatic $C_1$-$C_6$ and aromatic $C_6$-$C_{20}$ organic peracids and their percarboxylate forms;
d) organic peroxides;
e) oxidizing anions;
f) stable N-oxy (NO.) radicals;
g) hypervalent iodine derivatives;
h) organic compounds chosen from N-halosuccinimides, trichloroisocyanuric acid, N-hydroxyphthalimide, and alkyl nitrites;
i) hydrogen peroxide and systems which generate hydrogen peroxide, chosen from:
  i-1) urea hydrogen peroxide;
  i-2) polymer complexes which can release hydrogen peroxide;
  i-3) oxidases which produce hydrogen peroxide in the presence of a suitable substrate;
  i-4) metal peroxides which generate hydrogen peroxide in water;
  i-5) perborates; and
  i-6) percarbonates, and
j) combinations thereof.

16. The method according to claim 1, the method comprising applying, to the keratinous fibers, an aqueous composition comprising (a) at least one ortho-diphenol derivative, (b) at least one metal derivative, (c) at least one basifying agent, and optionally (d) at least one chemical oxidizing agent.

17. The method according to claim 1, the method comprising:
  (1) in a first stage, applying to the keratinous fibers a first composition comprising (a) at least one ortho-diphenol derivative, (b) at least one metal derivative; and optionally (d) at least one chemical oxidizing agent; and
  (2) in a second stage, subsequently applying to the keratinous fibers a second composition comprising (c) at least one basifying agent, wherein the second composition has a pH of greater than about 7.

18. The method according to claim 1, further comprising a post-treatment stage chosen from shampooing, rinsing, and/or drying of the keratinous fibers, optionally with heat treatment.

19. The method according to claim 1, further comprising subjecting the keratin fibers to photoirradiation by at least one electromagnetic wave having a wavelength ranging from 10 nm in the UV region and 100 μm in the infrared IR region.

20. A cosmetic composition for the dyeing of keratinous fibers, comprising:
  (a) at least one ortho-diphenol derivative;
  (b) at least one metal derivative chosen from metal salts, metal complexes, metal oxides, metal oxoanions, their supported forms, their hydrates and their mixtures, wherein the metal is chosen from:
    i) gold (Au),
    ii) molybdenum (Mo),
    iii) silver (Ag)(I) and (II),
    iv) tungsten (W),
    v) vanadium (V),
    vi) ruthenium (Ru),
    vii) magnesium (Mg)(II),
    viii) cerium (Ce),
    ix) rhenium (Re),
    x) titanium (Ti),
    xi) silicon (Si),
    xii) tin (Sn),
    xiii) zirconium (Zr),
    xiv) niobium (Nb),
    xv) indium (In),
    xvi) selenium (Se), and
    xvii) aluminium (Al), and
  (c) at least one basifying agent; and
  (d) optionally at least one chemical oxidizing agent.

* * * * *

UNITED STATES PATENT AND TRADEMARK OFFICE
CERTIFICATE OF CORRECTION

PATENT NO.      : 8,608,808 B2                    Page 1 of 1
APPLICATION NO. : 13/518862
DATED           : December 17, 2013
INVENTOR(S)     : Christophe Rondot et al.

It is certified that error appears in the above-identified patent and that said Letters Patent is hereby corrected as shown below:

In the Claims:

Claim 9, Col. 36, line 19, "6-diketone" should be -- β-diketone --.

Signed and Sealed this
Twenty-fifth Day of March, 2014

Michelle K. Lee
*Deputy Director of the United States Patent and Trademark Office*